US010737099B2

(12) United States Patent
Wasson et al.

(10) Patent No.: US 10,737,099 B2
(45) Date of Patent: Aug. 11, 2020

(54) ANTENNA FOR IMPLANTABLE MEDICAL DEVICES

(71) Applicant: Medtronic, Inc., Minneapolis, MN (US)

(72) Inventors: James R. Wasson, Tempe, AZ (US); Mark E. Henschel, Phoenix, AZ (US); Andrew J. Ries, Lino Lakes, MN (US); Rachel M. Day, Tempe, AZ (US); Kris A. Peterson, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 100 days.

(21) Appl. No.: 15/982,428

(22) Filed: May 17, 2018

(65) Prior Publication Data

US 2018/0333586 A1 Nov. 22, 2018

Related U.S. Application Data

(60) Provisional application No. 62/507,407, filed on May 17, 2017.

(51) Int. Cl.
*A61N 1/372* (2006.01)
*A61B 5/00* (2006.01)
*A61N 1/375* (2006.01)

(52) U.S. Cl.
CPC ........ *A61N 1/37229* (2013.01); *A61B 5/0031* (2013.01); *A61N 1/37205* (2013.01); *A61N 1/37282* (2013.01); *A61N 1/37512* (2017.08)

(58) Field of Classification Search
CPC .......................... A61N 1/37229; A61B 5/0031

USPC ........................................................ 607/32
See application file for complete search history.

(56) References Cited

U.S. PATENT DOCUMENTS

| 3,999,185 A | 12/1976 | Polgar, Jr. et al. |
| 4,724,381 A | 2/1988 | Crimmins |
| 5,117,824 A | 6/1992 | Keimel et al. |
| 5,167,626 A | 12/1992 | Casper et al. |
| 5,951,594 A | 9/1999 | Kerver |
| 6,028,558 A | 2/2000 | Van Voorhies |
| 6,931,284 B2 | 8/2005 | Engmark et al. |
| 7,282,045 B2 | 10/2007 | Houzego et al. |
| 7,558,620 B2 | 7/2009 | Ishibashi |
| 8,471,562 B2 | 6/2013 | Knizhnik |
| 8,543,190 B2 | 9/2013 | Wasson et al. |

(Continued)

FOREIGN PATENT DOCUMENTS

EP 3107148 A1 12/2016

OTHER PUBLICATIONS (PCT/US2018/033144) PCT Notification of Transmittal of the International Search Report and the Written Opinion of the International Searching Authority, dated Sep. 20, 2018, 11 pages.

(Continued)

*Primary Examiner* — Nadia A Mahmood

(57) ABSTRACT

Systems, devices and methods are disclosed that include an antenna for an implantable medical device, the antenna including a passageway extending through the antenna windings of the antenna, the passageway providing a pathway for an electrical connector providing at least one electrical connection between a power source and electronic circuitry included within the implantable medical device.

37 Claims, 16 Drawing Sheets

(56) References Cited

U.S. PATENT DOCUMENTS

| 9,588,148 B2 | 3/2017 | Cook et al. |
| 2011/0160557 A1 | 6/2011 | Cinbis et al. |
| 2012/0081201 A1* | 4/2012 | Norgaard ........... A61N 1/37229 336/96 |
| 2016/0213937 A1 | 7/2016 | Reinke et al. |

OTHER PUBLICATIONS

Jenison et al., "Implantable Medical Device Coil", U.S. Appl. No. 15/868,358, filed Jan. 11, 2018, 49 pages.

International Preliminary Report on Patentability from International Application No. PCT/US2018/033144, dated Nov. 28, 2019, 7 pp.

* cited by examiner

ANTENNA FOR IMPLANTABLE MEDICAL DEVICES

CROSS-REFERENCE TO RELATED APPLICATIONS

This application claims the benefit of U.S. Provisional Application Ser. No. 62/507,407, filed May 17, 2017, the entire contents of which are incorporated by reference herein.

TECHNICAL FIELD

The disclosure relates to medical device communication and, more particularly, to an antenna included within an implantable medical device.

BACKGROUND

Various implantable medical devices have been clinically implanted or proposed for therapeutically treating or monitoring one or more physiological and/or neurological conditions of a patient. Such devices may be adapted to monitor or treat conditions or functions relating to heart, muscle, nerve, brain, stomach, endocrine organs or other organs and their related functions. Advances in design and manufacture of miniaturized electronic and sensing devices have enabled development of implantable devices capable of therapeutic as well as diagnostic functions such as pacemakers, cardioverters, defibrillators, biochemical sensors, implantable loop recorders, and pressure sensors, among others. Such devices may be associated with leads that position electrodes or sensors at a desired location, or may be leadless with electrodes integrated into the device can. These devices may have the ability to wirelessly transmit data either to another device implanted in the patient or to another instrument located externally of the patient, or both.

Although implantation of some devices requires a surgical procedure, other devices may be small enough to be delivered and placed at an intended implant location in a relatively noninvasive manner, such as by a percutaneous delivery catheter or transvenously. By way of illustrative example, implantable miniature sensors have been proposed and used in blood vessels to measure directly the diastolic, systolic and mean blood pressures, as well as body temperature and cardiac output of a patient. As one example, patients with chronic cardiovascular conditions, particularly patients suffering from chronic heart failure, may benefit from the use of implantable sensors adapted to monitor blood pressures. As another example, subcutaneously implantable monitors have been proposed and used to monitor heart rate and rhythm, as well as other physiological parameters, such as patient posture and activity level. Such direct in vivo measurement of physiological parameters may provide significant information to clinicians to facilitate diagnostic and therapeutic decisions. In addition, miniaturized pacemakers that may be implanted directly within a patient's heart, with or without the need for external leads, have been proposed, built, and adapted to provide both pacing and other electrical therapy to the patient.

For most of these devices, the ability to communication with the device after implantation of the device, for example using wireless communication techniques, is important. The ability to communicate with the implanted device, for example to allow the device to be programmed and/or to communicate with other devices while the device is operating, may be important, and in some examples necessary, in order to carry out and to provide some or all of the intended functions and features available through the operation of the implanted medical device(s).

SUMMARY

The disclosure describes implantable medical devices, systems, and associated techniques, structures, and assemblies including or involving an antenna that may be used to provide communications between implantable medical devices and one or more other device(s). The implantable medical devices that include these antennas are often small devices that have been implanted relatively deeply within the patient, for example implanted internally with the heart of a patient. An example of such a device is the Medtronic® Micra® self-contained pacemaker that is designed to be implanted internally within the heart of a patient, and in various examples requires no external leads coupled to the device in order to provide pacing and electrical stimulation to the heart.

In some examples, the power source provided within the implantable medical device is not configured to be rechargeable following implantation of the device. Therefore, the overall mission lifespan of the device may be determined by and/or limited by the timespan over which the power source is able to provide adequate electrical power to operate the device. One solution to extend the mission lifespan of these implantable medical devices is to provide a larger power source, such as a larger size battery, in the device prior to implantation. However, a larger power source will generally be larger in size for a given same level of efficiency and a same energy density associated with a particular type of power source. In other words, a larger power source may require an increase in the overall size of implantable medical device.

Due to the need to miniaturize these implantable medical devices so that they may be implanted in the desired locations, such as within the heart, while maintaining a small size in order to minimize any obstruction, e.g., to blood flow, created by the device once implanted, an increase in the size of the power source, and thus the overall size of the implantable medical device, may be counter-productive for many applications. In addition to a larger power source, these implantable medical devices still need to include other components, such as electrical circuitry and an antenna, which are capable of allowing the device to perform the required telemetry and communications functions throughout the mission lifespan of the device. The systems, devices, and techniques described in this disclosure include an antenna and a power connection arranged to allow the electronic circuitry and the antenna to provide a required level of telemetry and communication functionality for the implanted medical device following implantation of the device, while using a more compact arrangement of these components that requires less space within the housing of the device.

By using less space and/or an efficient arrangement of the components, e.g., the electronic circuitry, the antenna, and/or the power connections within the device, a same size implantable medical device may be configured to include a larger power source, and thus have a longer mission lifespan compared to the same size device without the space saving and efficient arrange of the components as described in this disclosure. In addition to or in the alternative, by use of the space saving and efficient arrangement of the components as described in this disclosure, an implanted medical device having an overall smaller size, but for example with a same mission lifespan compared to a device without the space saving and efficient arrangement of these components, may be provided.

As described above, a longer mission lifespan and/or a smaller overall device size provides benefits to both the patient and the physicians/clinicians who install and/or treat the patient following the implantation of the devices. For example, a longer lifespan increases the time between when a device was implanted and when a replacement device may need to be implanted in the patient, and thus increases the time and/or may eliminate the need for the additional surgical process required to implant the replacement device. The miniaturization of the implantable medical device may allow for a less invasive implant procedure, such as implantation by use of a percutaneous delivery catheter or transvenously, to be used by the physician when implanting the device, and a smaller implant volume required within the patient following implantation. In addition, the antenna and arrangement of the antenna and other components as described in this disclosure may allow for a required level of telemetry and communications with the implantable medical device to be provided following implantation of the device while still providing one or more of the additional benefits, e.g. larger power source and/or smaller overall device size.

Examples described herein include an implantable medical device comprising: a power source configured to provide electrical power to the implantable medical device; an antenna comprising an axially symmetrical antenna winding that at least partially surrounds a passageway extending through the antenna winding along a longitudinal axis of the antenna; and a power connection electrically coupled to an electrical terminal of the power source, the power connection extending from a top surface of the power source into the passageway on a first side of the antenna, and forming an electrical connection with electronic circuitry located on a second side of the antenna opposite the first side of the antenna.

Examples described herein also include a communication device for an implantable medical device, the communication device comprising: an antenna comprising an axially symmetrical antenna winding comprising a plurality of windings of an electrical conductor surrounding a longitudinal axis of the antenna; and a passageway extending through the antenna winding along the longitudinal axis from a first side of the antenna to a second side of the antenna opposite the first side, the passageway configured to receive a power connection at the first side of the antenna, and to provide a pathway for the power connection to extend through the passageway to electrically couple the power connection to an electronic circuitry located on the second side of the antenna.

Examples described herein also include a method for operating an implantable medical device implanted within a patient, the method comprising: receiving electrical power, by a power connection, from a power source within the implanted medical device to power the electronic circuitry located within the implanted medical device, the power connection coupled to an electrical terminal of the power source and to the electronic circuitry; and communicating, by an antenna coupled to a communication circuitry, with one or more external devices using a signal that is transmitted from the antenna of the implanted medical device or that is received by the antenna of the implanted medical device; wherein the antenna comprises an axially symmetrical antenna winding that at least partially surrounds a passageway extending through the antenna winding along a longitudinal axis of the antenna, and wherein power connection electrically coupled to the electrical terminal of the power source extends from a top surface of the power source into the passageway on a first side of the antenna, and forms an electrical connection with the electronic circuitry, including the communication circuitry, located on a second side of the antenna opposite the first side of the antenna.

Examples described herein also include A method for assembling an implantable medical device, comprising: attaching an antenna winding to a circuit package including electronic circuitry, the antenna winding comprising a wound electrical conductor having a passageway extending through the antenna winding along a longitudinal axis of the antenna; and advancing the antenna winding and the circuit package toward an electrical power source including an electrical power connection extending from a top surface of the electrical power source so that the electrical power connection advances into the passageway of the antenna winding to form an electrical coupling with the electronic circuitry, wherein advancing the antenna winding toward the electrical power source includes advancing a bottom surface of the antenna toward the top surface of the electrical power source.

This summary is intended to provide an overview of the subject matter described in this disclosure. It is not intended to provide an exclusive or exhaustive explanation of the devices, systems, and methods described in detail within the accompanying drawings and description below. The details of one or more aspects of the disclosure are set forth in the accompanying drawings and the description below.

BRIEF DESCRIPTION OF THE FIGURES

The details of one or more examples of this disclosure are set forth in the accompanying drawings and the description below. Other features, objects, and advantages of this disclosure will be apparent from the description and drawings, and from the claims.

Figure 1:
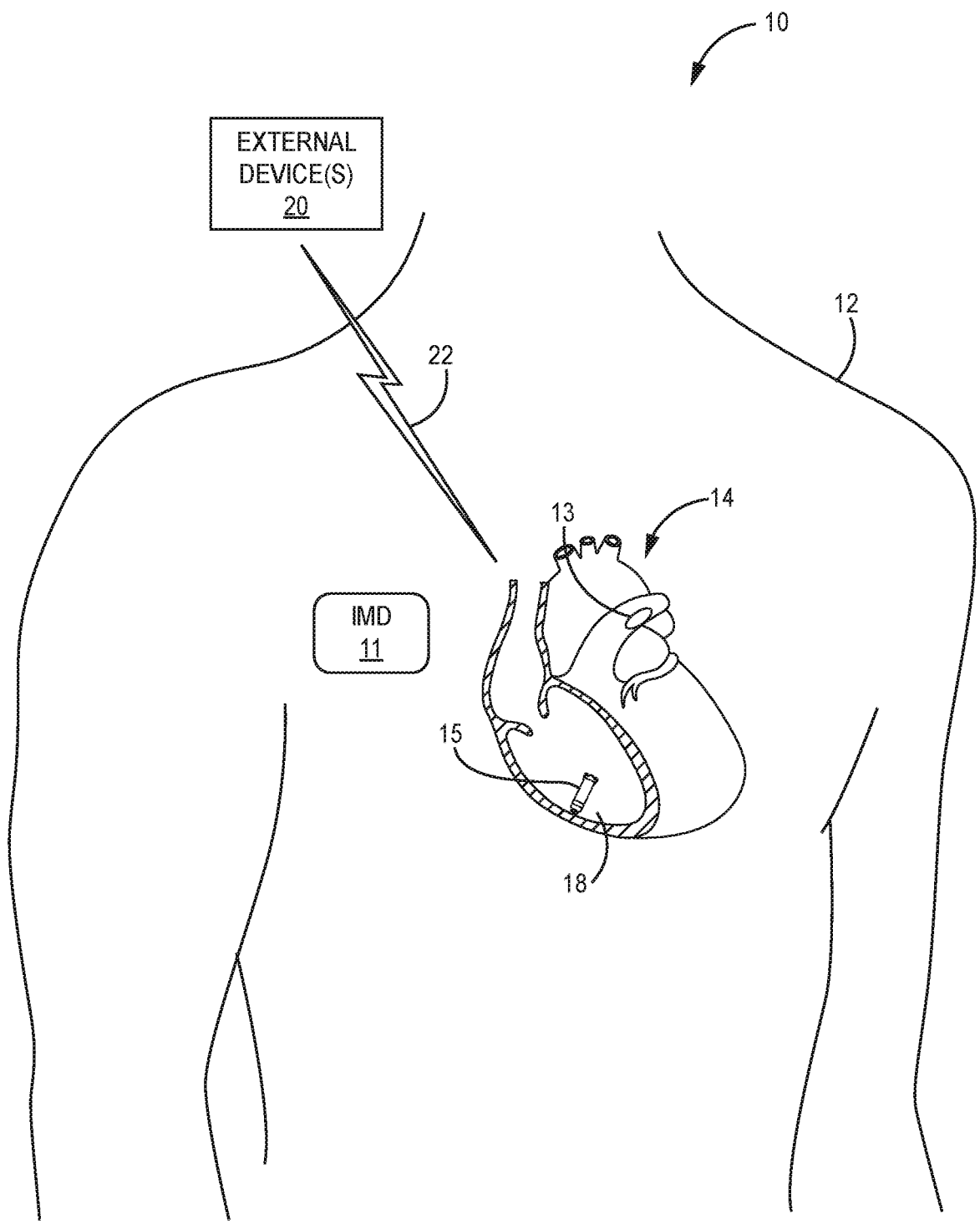
FIG. 1 is a conceptual drawing illustrating an example medical device system in conjunction with a patient according to various examples described in this disclosure.

In the figures, use of a same reference number or a same reference number with a letter extension may be used to indicate a same or corresponding device or element when used in a same drawing or in different drawings. In addition, unless otherwise indicated, devices and/or other objects such as a patient, an implantable medical device, or an electrical device such as an electrical coil, are not necessarily illustrated to scale relative to each other and/or relative to an actual example of the item being illustrated. In particular, various drawings provided with this disclosure illustrate a "patient" represented by a human-shaped outline, and are not to be considered drawn to scale relative to an actual human patient or with respect to other objects illustrated in the same figure unless otherwise specifically indicated in the figure for example by dimensional indicators, or for example as otherwise described in the text of the disclosure.

DETAILED DESCRIPTION

The desire for miniaturization, e.g., smaller overall size and/or smaller outside dimensions of implantable medical devices (IMDs) and an increase in the mission lifespan of these devices, especially devices that may not be recharged following implantation of the device, are often driven by parameters and/or characteristics of the device that compete with one another. For example, a larger power source provided within an IMD may increase the mission lifespan of the device, but may require an overall increase in the size of the IMD, and/or an increase in one or more exterior dimensions of the device. On the other hand, the need to miniaturize an IMD may require an overall reduction in the space within the IMD available for the power source, which may lead to a smaller power source being installed in the IMD, resulting in a shorter mission lifespan for the device. In some instances, in order to increase mission lifespan and/or to help reduce the overall size of the device, certain features and/or functions may be eliminated from the device, thus reducing for example the electrical power requirements of the device, but resulting in a device with a reduced level of features and/or functionality.

The devices, systems, and techniques described in this disclosure address many of the challenges associated with the tension between mission lifespans, miniaturization, and decisions regarding what features and/or functionality are to be provided by an IMD. These include providing a compact antenna that is coupled to communication circuitry included within the IMD, and arranged to provide the required level of telemetry and provide the communications functionality needed with the device following implantation of the device. The compact antenna in some examples is oriented so that a first surface of the antenna may be located adjacent to a top surface of the power source within the IMD, the antenna having a longitudinal passageway extending through the antenna windings that is configured to receive a power connection that is electrically coupled to the power source. The compact antenna may also be arranged to include a second surface of the antenna that may be located adjacent to a "puck" or other structure that includes the electronic circuitry used to operate the IMD and to provide the desired features and functions that the IMD is designed to provide following implantation of the device. The arrangement of the compact antenna allows the power connection to extend into and at least partially through the longitudinal passageway of the antenna, and to extend to the second surface of the antenna to provide an electrical connection between a first electrical terminal of the power source and the electrical circuitry included in the "puck." By arranging the power connection to extend through the passageway of the antenna, the space within the antenna included in the passageway, which would not necessarily provide a higher level of increased efficiency in the capabilities of the antenna if used for antenna windings, is instead used to provide a power connection between the power source and the electronic circuitry of the IMD. The placement of the first surface of the antenna adjacent to a top surface of the power source, and the second surface of the antenna adjacent to the to the "puck" including the electronic circuitry of the IMD, further eliminates unused spaces within the IMD, while providing a compact and efficient antenna arranged to occupy a minimum amount of space within the IMD.

The use of the antenna and/or the power connection, arranged according to the examples described in this disclosure, allow for a compact and space-efficient arrangement of these components within the IMD. These arrangements may free up space within a given size IMD that for example may then be used to provide a larger power source with the IMD. The larger power source may allow a longer mission lifespan for the IMD, and/or allow additional features/functions to be provided by a given size IMD, that might otherwise have to be left out of the IMD. In addition to or in the alternative, the free space created by use of the devices, systems, and techniques described this disclosure may also be removed from the design of the IMD to allow for further miniaturization of the IMD, for example allowing an IMD with an overall smaller size and/or smaller exterior dimension. The miniaturization of the IMD may be accomplished while still providing a device that has a same or longer mission lifespan, and/or may provide a same level of features/functions that could be provided in a larger size IMD.

FIG. 1 is a conceptual drawing illustrating an example of some components of a medical device system 10 in conjunction with a patient 12 according to various examples described in this disclosure. The systems, devices, and techniques described in this disclosure provide implantable medical devices (IMDs) that may include an antenna arranged in a manner further described throughout this disclosure, to communicatively link the IMD(s) with one or more external device(s) 20, and/or to each other, as further described below. System 10 may include a single IMD, such as IMD 15, implanted in patient 12. System 10 in some examples includes a plurality of IMDs, for example some combination of IMD 11, IMD 13, and/or IMD 15, as further described below. In various examples, at least one of the IMDs in system 10 includes an antenna configured as described in this disclosure, or any equivalents thereof. For purposes of this disclosure, knowledge of cardiovascular anatomy is presumed, and details are omitted except to the extent necessary or desirable to explain the context of the techniques of this disclosure.

As illustrated in FIG. 1, system 10 includes an intracardiac pacing device IMD 15. In the illustrated example, IMD 15 is implanted in the right-ventricle of patient 12, e.g., internal to the heart 14 of patient 12. In some examples, one or more IMDs (not specifically shown in FIG. 1) similar to IMD 15 may additionally or alternatively be implanted within other chambers of heart 14, or attached to the heart epicardially. IMD 15 may be configured to sense electrical activity of heart 14, and/or to deliver pacing therapy, e.g., bradycardia pacing therapy, cardiac resynchronization therapy (CRT), anti-tachycardia pacing (ATP) therapy, and/or post-shock pacing, to heart 14. IMD 15 may be attached to an interior wall 18 of heart 14 via one or more fixation mechanisms (not shown in FIG. 1, but for example fixation mechanisms 42, 44 shown in FIG. 2) that penetrate the tissue. As shown in FIG. 1, the fixation mechanisms may secure IMD 15 to the cardiac tissue and retain an electrode (e.g., a cathode or an anode) on the housing of IMD 15 in contact with the cardiac tissue. In addition to delivering pacing pulses, IMD 15 may be capable sensing electrical signals using the electrodes carried on the housing of IMD 15. These electrical signals may be electrical signals generated by cardiac muscle and indicative of depolarizations and repolarizations of heart 14 at various times during the cardiac cycle.

In various examples, IMD 15 is configured to wirelessly communicate with one or more external device(s) (20) as illustratively shown in FIG. 1 by communication link 22. External device(s) 20 may be a computing device, e.g., used in a home, ambulatory, clinic, or hospital setting, to wirelessly communicate with IMD 15. External device(s) 20 may be coupled to a remote patient monitoring system, such as Carelink®, available from Medtronic plc, of Dublin, Ireland. External device(s) 20 may be, as examples, a programmer, external monitor, or consumer device, e.g., smart phone. External device(s) 20 may be used to program commands or operating parameters into IMD 15 for controlling the functioning of IMD 15. External device(s) 20 may be used to interrogate IMD 15 to retrieve data, including device operational data as well as physiological or neurological data accumulated in memory of IMD 15. The interrogation may be automatic, e.g., according to a schedule, or in response to a remote or local user command. One or more of these external device(s) 20 may also be referred to as an "instrument" or as a group of instruments.

Examples of communication techniques used by IMD 15 and external device(s) 20 are not limited to any particular communication technique or communication protocol, and in some examples include tissue conductance communication (TCC) or RF telemetry, which may be an RF link established via Bluetooth®, WiFi, or medical implant communication service (MICS). IMD 15 may utilize an antenna arranged as described in this disclosure, or an equivalent thereof, to perform the communications associated with IMD 15, in order to provide any of the features and to perform any of the functions ascribed to IMD 15.

In order to provide electrical power to IMD 15 so that IMD 15 may perform the functions and provide the features ascribed to the IMD, an internal electrical power source, (not shown in FIG. 1, but for example power source 63 shown in FIG. 3), may be included within IMD 15. The power source included within IMD 15 may be a battery. In various examples of IMD 15, the power source may or may not be rechargeable following implantation of the IMD within a patient while the IMD remains implanted. As noted above, a primary (non-rechargeable) battery has a finite energy reservoir which limits its mission life based on its size and energy density (for a given energy usage rate). Therefore, a larger size battery (for a given energy density and a given energy usage rate) may potentially allow a longer mission lifespan for an implanted IMD, in particular in instances of IMDs that are not configured for example to be recharged while the IMD remains implanted within the patient. However, a larger battery size also may lead to an increase in the overall size of the IMD.

Due to the need to miniaturize the IMD devices so that they may be implanted in the desired locations, such as within the heart, while maintaining a small size in or to minimize any obstruction, e.g., to blood flow created by the device once implanted, the antenna configurations described in this disclosure may allow for an increase in the size of the power source provided with an IMD, but in some examples without an increase in the overall size of the IMD. This feature may allow the IMD to provide, potentially, a longer mission life utilizing a same size IMD, based on the larger sized power supply and the antenna arrangement described herein. In the alternative, a same size power source may be used with an example of the antenna arrangement described herein, or any equivalent thereof. In these examples, arrangement of the antenna as describe herein may allow for an even smaller sized IMD to be provide that has a mission lifespan at least equal to the mission lifespan provided by the larger sized IMDs using other antenna arrangements, which require more space within the IMD, to provide the required communications with the IMD.

Referring again to FIG. 1, in various examples system 10 includes one or more additional IMDs, such as IMD 11 and/or IMD 13, that may be implanted in various locations of patient 12 outside the ventricles of heart 14 of patient 12. IMD 11 is illustrative of one or more implanted devices, such as one or more implantable monitoring device, an implantable hub device, or implantable loop recorder. Examples of IMD 11 may include an insertable cardiac monitor (ICM) capable of sensing and recording cardiac electrogram (EGM) (also referred to as an electrocardiogram, ECG, or EKG when external electrodes are placed on the skin) signals from a position outside of heart 14 via electrodes (not shown in FIG. 1). In some examples, IMD 11 includes or is coupled to one or more additional sensors, such as accelerometers, that generate one or more signals that vary based on patient motion and/or posture, blood flow, or respiration. Examples of IMD 11 may monitor a physiological parameter indicative of patient state, such as posture, heart rate, activity level, and/or respiration rate. IMD 11 may be implanted outside of the thorax of patient 12, e.g., subcutaneously or submuscularly, such as the pectoral location illustrated in FIG. 1. In some examples, IMD 11 may take the form of a Reveal LINQ® ICM, available from Medtronic plc, of Dublin, Ireland. In other examples, IMD 11 may be a pacemaker, e.g., configured to sense electrical activity of heart 14, and/or to deliver pacing therapy, e.g., bradycardia pacing therapy, cardiac resynchronization therapy (CRT), anti-tachycardia pacing (ATP) therapy, and/or post-shock pacing, to heart 14, e.g., via intracardiac or extracardiac leads (not shown), and/or a cardioverter/defibrillator configured to detect tachyarrhythmias and deliver anti-tacharrhythmia shocks to heart 14 via the one or more leads.

In various examples, one or more of the IMDs illustratively shown as IMD 11 in FIG. 1, may include the antenna arranged in accordance with the examples of antenna described in this disclosure, and any equivalents thereof, to facilitate the communications with the one or more IMDs of system 10, and/or between the one or more IMDs 11, IMD 13, IMD 15, and/or external device(s) 20. In various examples, monitoring and/or delivery of therapy by IMD 11 may be provided in conjunction with the features and functions provided by IMD 15. In some examples, IMD 15 may engage in wireless communications between IMD 15 and one or more other IMD(s) 11 and/or IMD 13 to facilitate coordinated activity between IMD 15 and these one or more other IMD(s). The wireless communication may by via TCC of radio-frequency (RF) telemetry, and may be one-way communication in which one device is configured to transmit communication messages and the other device is configured to receive those messages, or two-way communication in which each device is configured to transmit and receive communication messages.

IMD 13 as shown in FIG. 1, may comprise an implantable pressure sensing device that may be implanted within pulmonary artery of the patient. In some examples, the pulmonary artery may comprise a left pulmonary artery, whereas in other examples, pulmonary artery may comprise a right pulmonary artery. For the sake of clarity, a fixation assembly for IMD 13 is not depicted in FIG. 1.

As illustrated in FIG. 1, IMD 13 may be implanted, as one example, within a pulmonary artery of patient 12, and may include pressure sensing circuitry configured to measure the cardiovascular pressure within the pulmonary artery of patient 12. In some examples, IMD 13 may include wireless communication circuitry. e.g., TCC and/or RF telemetry circuitry, configured to receive a trigger signal from IMD 11 and/or IMD 15, at electrodes or an antenna provided in IMD 13. The pressure sensing circuitry of IMD 13 may be configured to measure the cardiovascular pressure of patient 12 in response to receiving the trigger signal. In either case, IMD 13 may be configured to transmit the measured pressure values to IMD 11 and/or IMD 15 by wireless communication. For example, IMD 13 may transmit measurements and data acquired by IMD 13 related to pulmonary artery pressure and other information generated by IMD 13 to IMD 11, to IMD 15, and/or to external device(s) 20. In various examples, IMD 13 comprises an antenna used for communications between IMD 13 and other devices of system 10, arranged using the examples of antennas described throughout this disclosure, or any equivalents thereof.

For the remainder of the disclosure, a general reference to a medical device system may refer collectively to include any examples of medical device system 10, as described above with respect to FIG. 1, and any equivalents thereof. Further, for the remainder of the disclosure a general reference to an IMD may refer collectively to include any examples of IMD 11, IMD 13, and/or IMD 15, as described above with respect to FIG. 1, and any equivalents thereof.

Figure 2:
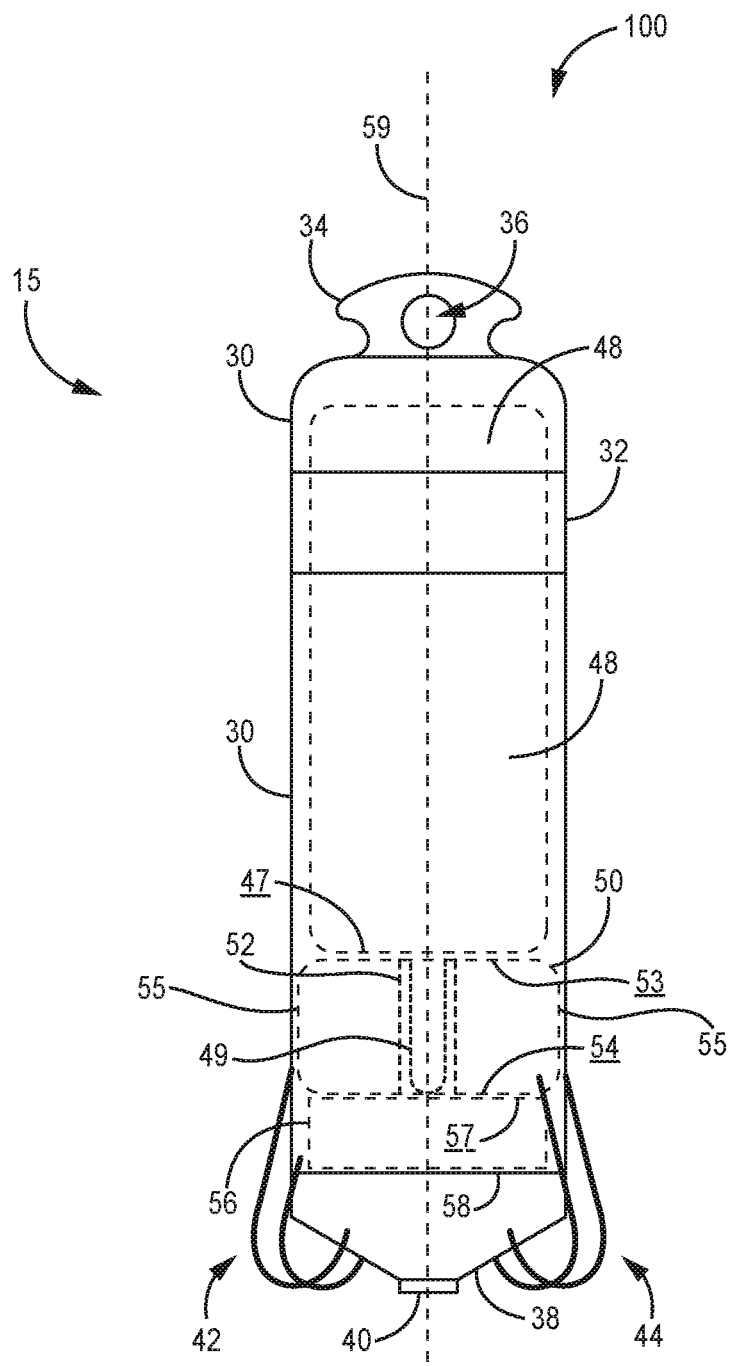
FIG. 2 is a diagram of an implantable medical device, e.g., an intracardiac pacing device, according to various examples described in this disclosure.

FIG. 2 is a diagram of an IMD, such as IMD 15, e.g., an intracardiac pacing device, according to various examples described in this disclosure. In some examples, IMD 15 is a Medtronic® Micra® Transcathether Pacing System developed by Medtronic, plc, of Dublin, Ireland. IMD 15 may be configured to be implanted in the left ventricle of the heart of a patient, as depicted in FIG. 1. IMD 15 is an example of an implantable medical device that may include an antenna configured according to any of the examples described in this disclosure, or any equivalents thereof.

As shown in FIG. 2, IMD 15 includes case 30, flange 34, opening 36, cap 38, case electrode 32, tip electrode 40, and fixation mechanisms 42 and 44. IMD 15 as shown in FIG. 2 also includes electronic circuitry 56 including communication circuitry coupled to an antenna 50, and a power source 48, for example a battery, that is coupled to the electronic circuitry and configured to provide power to the electronic circuitry. Antenna 50 may be electrically coupled to the communication circuitry of electronic circuitry 56, for example via the ends of an electrical conductor used to form the windings of antenna 50. Communication circuitry of IMD 15 may be configured to provide wireless communications between IMD 15 and other devices, such as one or more of external device(s) 20, and/or additional IMDs, as illustrated and described with respect of FIG. 1. In various examples, the configuration of antenna 50 as shown in FIG. 2 is arranged to provide efficient wireless communication using a predetermined frequency or range of frequencies, for example wireless communication based on a carrier frequency of up to 175 kHz. Antenna 50 may also be configured to provide efficient communication based on a particular wireless communications format, for example wireless communication based on a telB communication format.

To save space and keep IMD 15 as small as possible, antenna 50 may be formed from windings of an electrical conductor formed around a passageway 52, the passageway 52 forming an opening that passes through the windings of the antenna along a longitudinal axis 59 of the IMD and antenna 50. Antenna 50 may be arranged, for example with respect to the windings of the electrical conductor used to form the antennas, to maximize performance at the predetermined frequencies and/or based on a particular communication format. As shown in FIG. 2, at least one power connection e.g., power connector 49, is electrically coupled to one terminal, e.g., a first polarity, of the electrical power provided by power source 48. Power connector 49 extends from the power source 48 through the passageway 52, and contacts an electrical contact area of the electronic circuitry 56. By providing power connector 49 in a portion of the area surrounded by antenna 50 and forming passageway 52, power connector 49 is provided in an area within IMD 15 where additional winding, if present as part of antenna 50, would add less efficiency to the antenna compared to winding of antenna 50 provided in the areas actually occupied by antenna 50 within IMD 15. As such, the power connection provided by power connector 49 between power source 48 and electronic circuitry 56 may be made using space that would not necessarily provide a significant efficiency increase with respect to the performance characteristics of antenna 50 if utilized for additional winding of the antenna.

In addition, the arrangement of antenna 50 within IMD 15 and relative to power source 48 and electronic circuitry 56 also may minimize the amount of space required for antenna 50 while still providing an antenna that provides the required level of communications capabilities for the IMD. As shown in FIG. 2, antenna 50 is arranged in a generally cylindrical shape, having a plurality of windings (not specifically shown in FIG. 2) formed of an electrical conductor, such as a metallic wire, wound in a substantially symmetrical manner around passageway 52. The antenna winding may be considered to by axially symmetrical in that the winding of the antenna would be symmetrical in any cross-section formed by any plane cutting antenna 50 that also includes longitudinal axis 59 as being coplanar to the cutting plane. The windings of the antenna 50 as shown in FIG. 2 provides a bottom surface 53 that substantially a flat surface perpendicular to longitudinal axis 59, and provides a top surface 54 that is substantially a flat surface perpendicular to longitudinal axis 59, and wherein bottom surface 53 and top surface 54 are formed in parallel planes relative to one another and on opposite sides of the antenna. The windings of the electrical conductor forming antenna 50 are formed between bottom surface 53 and top surface 54, and surround passageway 52 to form the generally circular cylindrical shape of antenna 50.

As shown in FIG. 2, the bottom surface 53 of antenna 50 is located adjacent to, and in some examples in contact with at least over some portion or portions of bottom surface 53, a top surface 47 of power source 48. Using this arrangement, a minimum amount of space within IMD 15 is required between power source 48 and the bottom surface 53 of antenna 50. In a similar manner, the top surface of antenna 50 is located adjacent to, and in some examples is in contact with at least over some portion or portion of the top surface 54, a bottom surface 57 of electronic circuitry 56. In some examples, electronic circuitry 56 is provided on a circuit package 58 or other structure, such as a circuit board, wafer scale, or a circuit package, that forms the bottom surface 57 of the electronic circuitry 56. Using this arrangement, a minimum amount of space within IMD 15 is required between the top surface 54 of antenna 50 and the bottom surface 57 of electronic circuitry 56.

Figure 4A:
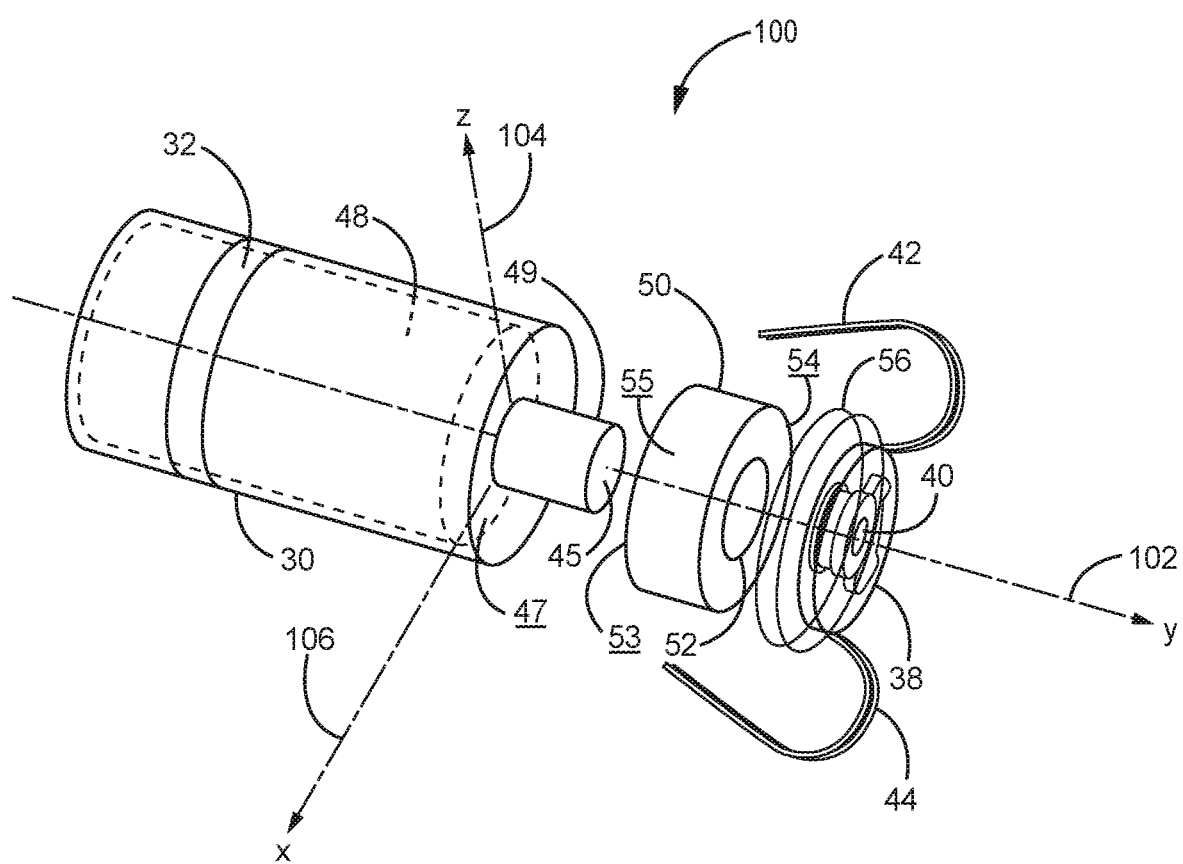
FIG. 4A is an exploded view of an example IMD according to various examples described in this disclosure.
Figure 4B:
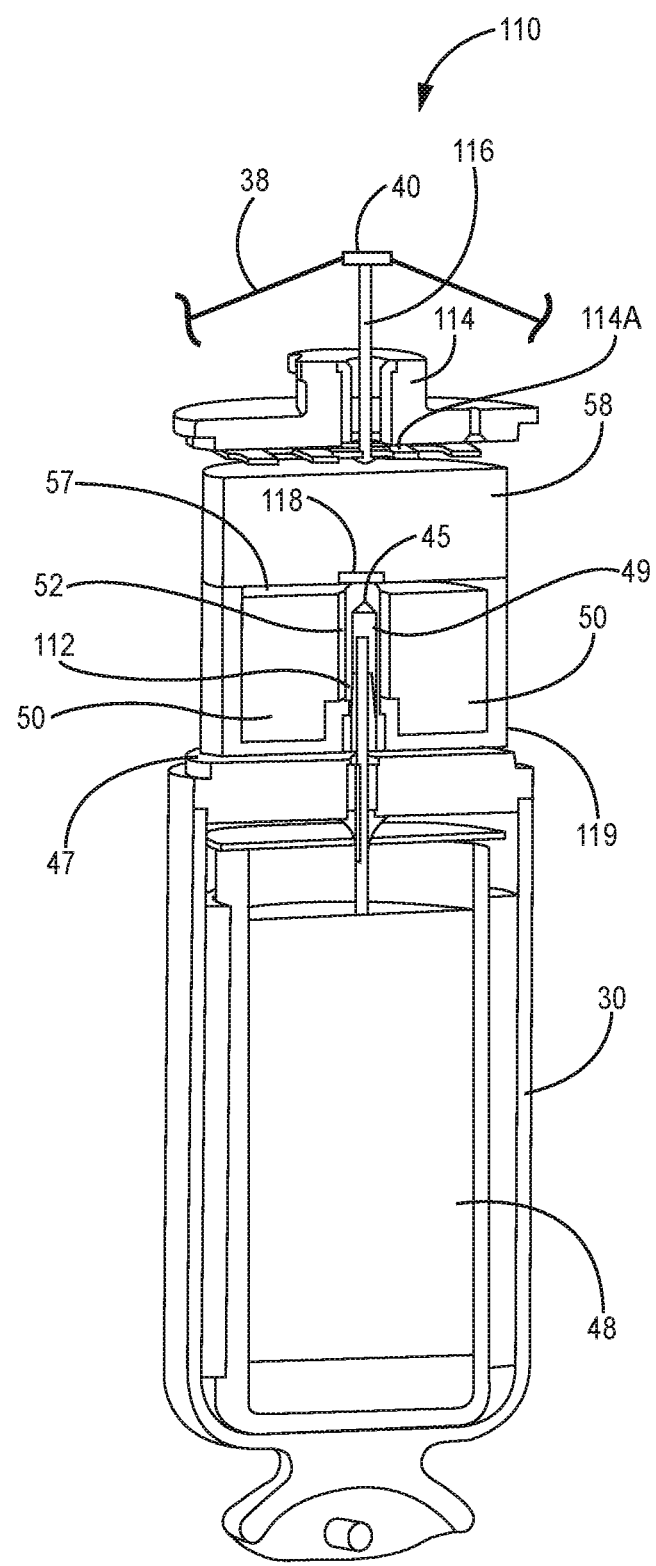
FIG. 4B is a cutaway view of an example IMD according to various examples described in this disclosure.
Figure 4C:
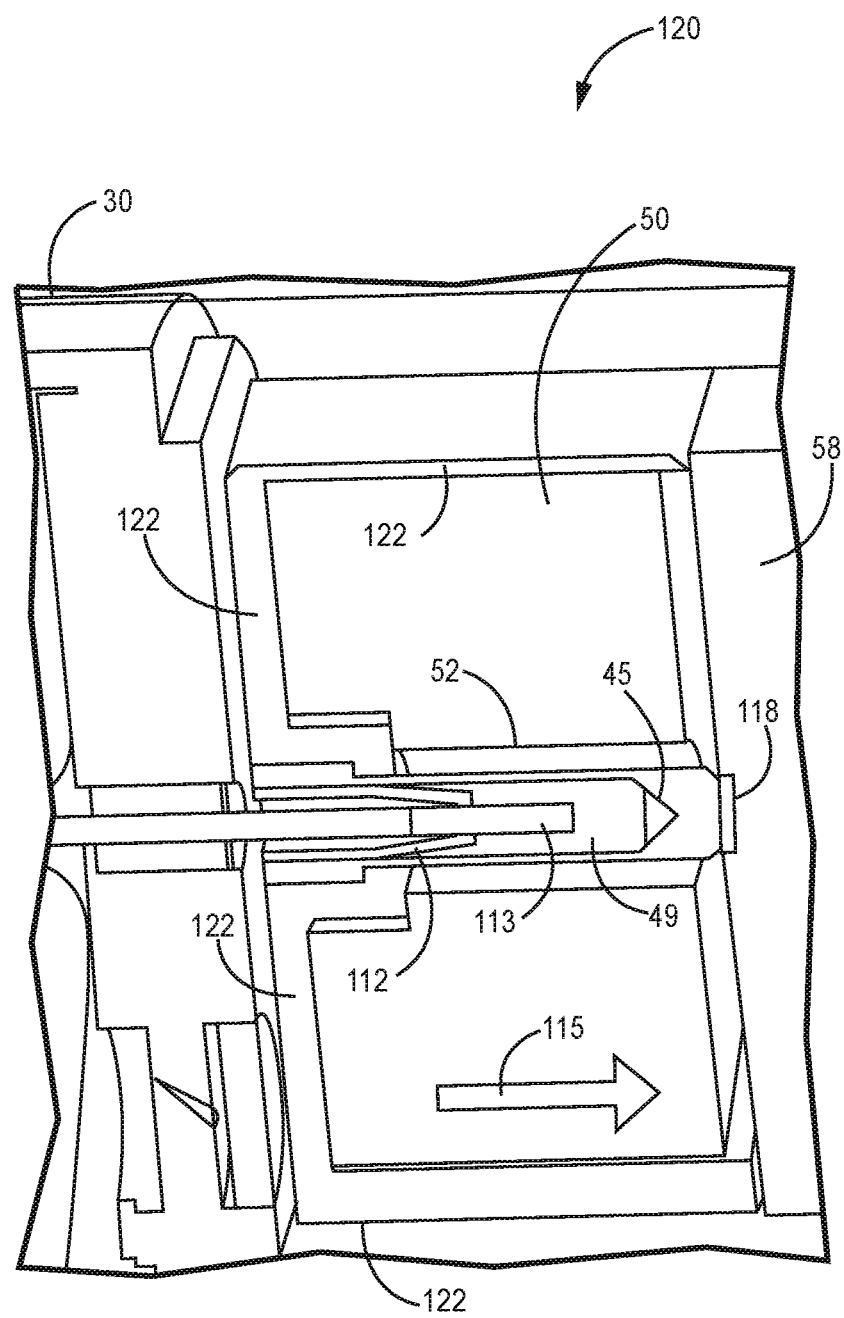
FIG. 4C is another cutaway view of an example IMD 15 according to various examples described in this disclosure.

In various examples, the windings forming antenna 50 may be provided on a coil form (not specifically shown in FIG. 2, but for example coil form 119, 122 illustrated and described with respect to FIGS. 4B, 4C, respectively). In various examples, the coil form includes a structure, formed for example of a plastic material, that provides a shape that supports the windings of antenna 50 in the cylindrical shape illustrated in FIG. 2. In some examples, the coil form provides an inner hollow shape that provides the passageway 52 extending from the bottom side 53 to the top surface 54 of antenna 50. In some examples, the coil form may provide some or all of the surfaces indicated as the bottom surface 53 of antenna 50, and/or may provide some or all of the surface indicated as the top surface 54 of antenna 50.

Regardless of whether antenna 50 includes or does not include a coil form, the windings used to form antennas 50 may extend to an outer surface 55 of the antenna. The outer surface 55 of antenna may in some examples be comprised of the outermost layer of the windings of the electrical conductor forming antenna 50. As shown in FIG. 2, the dimension of the antenna may be arranged so that the outer surface 55 of antenna extents to a position adjacent to the inside of case 30. In some examples where case 30 is formed from an electrically conductive material, a thin layer of insulative material (not shown in FIG. 2) may be provided between outer surface 55 and the case 30 to prevent possible electrically shorting between the antenna and the case. As shown in FIG. 2, the dimension of antenna 50 may be configured to utilize the space within case 30 without unused space around and surrounding antenna 50, while still accommodating space, using passageway 52, to allow for the electrical connection between power source 48 and electronic circuitry 56 as provided by power connector 49.

In various examples, the power connector 49 extending from power source 48 provides the positive terminal of the direct current (DC) electrical power provide by power source 48. The electrical connection provided by power connector 49 electrically couples the electronic circuitry 56 to a first polarity of the electrical power provided by power source 48. In various examples, electronic circuitry 56 is electrically coupled to the cap 38 and/or case 30, which is also electrically coupled to a second terminal, e.g., a negative terminal, of power source 48. This electrical connection between electronic circuitry 56 and the cap 38 and/or case 30 in some examples provides the return circuit path for the electrical current flowing from power source 48 to the electronic circuitry 56 of IMD 15.

In various examples, tip electrode 40 of IMD 15 is electrically coupled to electronic circuitry 56, and may be coupled through electronic circuitry 56 to provide electrical power to the tip electrode in the form of electrical stimulation and therapy, to the tissue of the patient that may be brought into contact with tip electrode 40. In various examples, fixation mechanisms 42, 44, and/or electrode 32 of IMD 15 may be configured to provide a return path for electrical currents transmitted to the tissue of the patient via tip electrode 40.

As described above, IMD 15 includes case 30, cap 38, tip electrode 40, case electrode 32, fixation mechanisms 42 and 44, flange 34, and opening 36. Together, case 30 and cap 38 may be considered the housing of IMD 15. In this manner, case 30 and cap 38 may enclose and protect the various electrical components, e.g., power source 48, antenna 50, and electronic circuitry 56, within IMD 15. In some examples, case 30 may enclose substantially all of the electrical components, and cap 38 may seal case 30 and create the hermetically sealed housing of IMD 15. Although IMD 15 is generally described as including one or more electrodes, IMD 15 may typically include at least two electrodes (e.g., electrodes 32 and 40) to deliver an electrical signal (e.g., therapy such as cardiac pacing) and/or provide at least one sensing vector.

Electrodes 32 and 40 may be carried on the housing created by case 30 and cap 38. In this manner, electrodes 32 and 40 may be considered leadless electrodes. In the example of FIG. 2, tip electrode 40 is disposed on the exterior surface of cap 38. Tip electrode 40 may be a circular electrode positioned to contact cardiac tissue upon implantation. Case electrode 32 may be a ring or cylindrical electrode disposed on the exterior surface of case 30. Both case 30 and cap 38 may be an electrically insulating material, or otherwise electrically insulated relative to electrodes 32 and 40.

Electrode 40 may be used as a cathode and electrode 32 may be used as an anode, or vice versa, for delivering cardiac pacing such as bradycardia pacing, CRT, ATP, or post-shock pacing. However, electrodes 32 and 40 may be used in any stimulation configuration. In addition, electrodes 32 and 40 may be used to detect intrinsic electrical signals from cardiac muscle. Tip electrode 40 may be configured to contact cardiac tissue such as an interior wall of the left ventricle of a patient.

Fixation mechanisms 42 and 44 may attach IMD 15 to cardiac tissue when IMD 15 is implanted within a patient. Fixation mechanisms 42 and 44 may be active fixation tines, screws, clamps, adhesive members, or any other mechanisms for attaching a device to tissue. As shown in the example of FIG. 2, fixation mechanisms 42 and 44 may be constructed of a memory material, such as a shape memory alloy (e.g., nickel titanium), that retains a preformed shape. During implantation, fixation mechanisms 42 and 44 may be flexed forward to pierce tissue and allowed to flex back towards case 30. In this manner, fixation mechanisms 42 and 44 may be embedded within the target tissue. In various examples, IMD 15 includes a set of 4 tines as fixation mechanisms 42, 44. In alternative examples, IMD 15 may include more or less tines, for example two or three tines are contemplated.

Flange 34 may be provided on one end of case 30 to enable tethering or extraction of IMD 15. For example, a suture or other device may be inserted around flange 34 and/or through opening 36 and attached to tissue. In this manner, flange 34 may provide a secondary attachment structure to tether or retain IMD 15 within the heart of a patient, for example as a redundant fixation mechanism in case fixation mechanisms 42 and/or 44 fail. Flange 34 and/or opening 36 may also be used to extract IMD 15 once the IMD needs to be explanted (or removed) from the patient if such action is deemed necessary. IMD 15 is one example of a pacing device configured to include one or more electrodes according to this disclosure. However, other implantable medical devices may be configured to include one or more electrodes similar to those described with respect to IMD 15.

Using the arrangement of the power connector 49, antenna 50, passageway 52, and electronic circuitry 56 as shown in FIG. 2, a more compact arrangement of these devices, requiring less space within the device, may be provided. The reduction in the required space may in some examples allow for a larger power source 48 to be provide as part of IMD 15. A larger power source 48 may increase the overall useful mission lifespan of IMD 15, for example by years in some cases, especially in devices where power source 48 cannot be recharged at any point in time while the device is implanted in a patient. Further, the compact arrangement of the power connector 49, antenna 50, passageway 52, and the electronic circuitry 56 may allow for a device having a same or smaller power source 48, thus allowing for an overall smaller IMD to be provided based on the more efficient arrangement of other components as illustrated in FIG. 2. Additional examples and details regarding the arrangement of the components provided in various examples of IMD 15 are illustrated and described in further detail below with respect to FIGS. 3, 4A-F, and 5.

Figure 3:
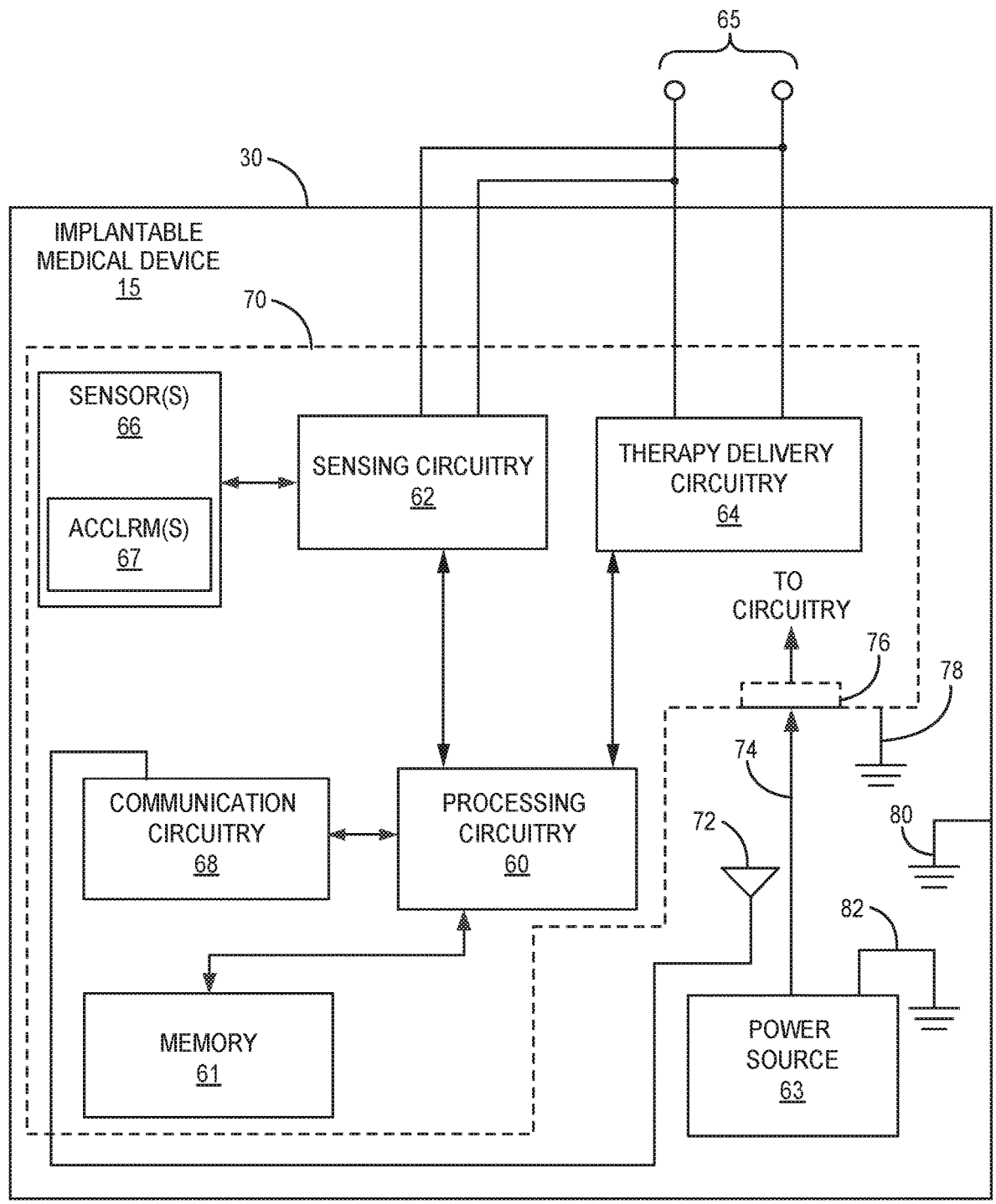
FIG. 3 is a functional block diagram illustrating an example configuration of an IMD according to various examples described in this disclosure.

FIG. 3 is a functional block diagram illustrating an example configuration of an IMD 15 according to various examples described in this disclosure. IMD 15 may correspond to any of the IMD(s), or portions thereof, illustrated and described with respect to FIGS. 1, 2, 4A-4F and 5. As shown in FIG. 3, IMD 15 includes a power source 63 that is coupled to the electronic circuitry 70 provided in IMD 15, and is configured to provide electrical power to the devices of electronic circuitry 70. Electrical circuitry 70 as shown in FIG. 3 includes processing circuitry 60, memory 61, sensing circuitry 62, therapy delivery circuitry 64, and sensors 66. Sensors 66 may include one or more position and/or motion sensing sensors, such as accelerometer(s) 67. Electronic circuitry 70 also includes communication circuitry 68 coupled to antenna 72. Antenna 72 may be arranged as an antenna having a passageway passing through the antenna winding of the antenna along a longitudinal axis of the antenna, as described throughout this disclosure, and any equivalents thereof.

The electronic circuitry 70 and devices included in electronic circuitry 70 may be provided on a structure, such as puck, such as circuit package 58 illustrated and describe with respect to FIGS. 2 and 4A-4E. As shown in FIG. 3, power source 63 includes a power connection 74 that is electrically connected to one terminal (voltage level) of power source 63. In various examples, power connection 74 is power connector 49 illustrated and described with respect to FIGS. 2 and 4A-4E. As illustratively shown in FIG. 3, power connection 74 passes through the electrical conductor forming antenna 72 in the portion of the power connection 74 between power source 63 and an electrical contact 76 of electronic circuitry 70. Electrical contact 76 may be electrically coupled to the electrical conductors and electronic devices of electronic circuitry 70, and configured to provide a flow of current provided by power source 63 and flowing through power connection 74 to electronic circuitry 70. In various examples, connection 78 may be electrically coupled to a reference voltage 82, (second terminal) of power source 63, to provide one return path for current provided to electronic circuitry 70 from power source 63. In various examples, connection 78 is coupled to the case 30 of IMD 15, wherein the case is coupled to reference voltage 82 of power source 63, thus using case 30 of IMD 15 as a return path for current provided to power electronic circuitry 70 from power source 63.

In the illustrated example, IMD 15 includes processing circuitry 60 and an associated memory 61, sensing circuitry 62, therapy delivery circuitry 64, one or more sensors 66, and the communication circuitry 68 coupled to antenna 72, as described above. However, IMD 15 need not include all of these components, or may include additional components. For example, some examples of IMD 15 that do not provide therapy, therapy delivery circuitry 64 may not be included in IMD 15.

Memory 61 includes computer-readable instructions that, when executed by processing circuitry 60, cause IMD 15 and processing circuitry 60 to perform various functions attributed to IMD 15 and processing circuitry 60 herein. (e.g., preparing and transmitting from IMD 15 information and data by wireless communication using communication circuitry 68 and antenna 72 prepared by processing circuitry 60, and receiving at antenna 50 and through communication circuitry 68, a wireless communications, and processing the received communications for example using processing circuitry 60). Memory 61 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital or analog media. Memory 61 may store threshold(s) for time of day, posture, heart rate, activity level, respiration rate, and other parameters. Memory 61 may also store data indicating cardiovascular pressure measurements. Memory 61 may store data, instructions, and/or parameters for use by processing circuitry 60 and/or communication circuitry 68 in performing the telemetry and communication functions of the IMD. Processing circuitry 60 may be configured to access data and/or instructions stored in memory 61 in order to perform any of the function and provide any of the features ascribed to IMD 15 throughout this disclosure, and any equivalents thereof.

Processing circuitry 60 may include fixed function circuitry and/or programmable processing circuitry. Processing circuitry 60 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 60 may include multiple components, such as any combination of one or more microprocessors, one or more controllers, one or more DSPs, one or more ASICs, or one or more FPGAs, as well as other discrete or integrated logic circuitry. The functions attributed to processing circuitry 60 herein may be embodied as software, firmware, hardware or any combination thereof.

Sensing circuitry 62 and therapy delivery circuitry 64 are coupled to electrodes 65. Electrodes 65 illustrated in FIG. 3 may correspond to electrodes 32 and 40 of IMD 15 (FIG. 2). Sensing circuitry 62 may monitor signals from a selected two or more of electrodes 65 in order to monitor electrical activity of heart, impedance, or some other electrical phenomenon. Sensing of a cardiac electrical signal may be done to determine heart rates or heart rate variability, or to detect arrhythmias (e.g., tachyarrhythmias or bradycardia) or other electrical signals. In some examples, sensing circuitry 62 may include one or more filters and amplifiers for filtering and amplifying a signal received from electrodes 65. In some examples, sensing circuitry 62 may sense or detect physiological parameters, such as heart rate, blood pressure, respiration, and other physiological parameters associated with a patient.

The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter. Sensing circuitry 62 outputs an indication to processing circuitry 60 in response to sensing of a cardiac event (e.g., detected P-waves or R-waves).

In this manner, processing circuitry 60 may receive detected cardiac event signals corresponding to the occurrence of detected R-waves and P-waves in the respective chambers of heart. Indications of detected R-waves and P-waves may be used for detecting ventricular and/or atrial tachyarrhythmia episodes, e.g., ventricular or atrial fibrillation episodes. Some detection channels may be configured to detect cardiac events, such as P- or R-waves, and provide indications of the occurrences of such events to processing circuitry 60, e.g., as described in U.S. Pat. No. 5,117,824 to Keimel et al., which issued on Jun. 2, 1992 and is entitled. "APPARATUS FOR MONITORING ELECTRICAL PHYSIOLOGIC SIGNALS," and is incorporated herein by reference in its entirety.

Sensing circuitry 62 may also include a switch module to select which of the available electrodes 65 (or electrode polarities) are used to sense the heart activity. In examples with several electrodes 65, processing circuitry 60 may select the electrodes that function as sense electrodes, i.e., select the sensing configuration, via the switch module within sensing circuitry 62. Sensing circuitry 62 may also pass one or more digitized EGM signals to processing circuitry 60 for analysis, e.g., for use in cardiac rhythm discrimination.

In the example of FIG. 3, IMD 15 includes one or more sensors 66 coupled to sensing circuitry 62. Although illustrated in FIG. 3 as included within IMD 15, one or more of sensors 66 may be external to IMD 15, e.g., coupled to IMD 15 via one or more leads, or configured to wirelessly communicate with IMD 15. In some examples, sensors 66 transduce a signal indicative of a patient parameter, which may be amplified, filtered, or otherwise processed by sensing circuitry 62. In such examples, processing circuitry 60 determines values of patient parameters based on the signals. In some examples, sensors 66 determine the patient parameter values, and communicate them, e.g., via a wired or wireless connection, to processing circuitry 60.

In some examples, sensors 66 include one or more accelerometers 67, e.g., one or more three-axis accelerometers. Signals generated by the one or more accelerometers 67 may be indicative of, as examples, gross body movement (e.g., activity) of the patient, patient posture, heart sounds or other vibrations or movement associated with the beating of the heart, or coughing, rales, or other respiration abnormalities. Accelerometers 67 may produce and transmit signals to processing circuitry 60 for a determination as to in the posture of the patient. In various examples, signals from the accelerometers 67 are processed to determine an activity, such as when the patient is taking a step or steps, or for example when the patient is running, used to provide an activity count associated with patient initiated physical activity of the patient. In some examples, sensors 66 may include sensors configured to transduce signals indicative of blood flow, oxygen saturation of blood, or patient temperature, and processing circuitry 60 may determine patient parameters values based on these signals. In various examples, sensors 66 may include one or a combination of sensors 19 as previously described.

In some examples, processing circuitry 60 determines one or more patient parameter values based on pressure signals. Patient parameter values determined based on pressure may include, as examples, systolic or diastolic pressure values, such as pulmonary artery diastolic pressure values. In some examples, a separate device (such as IMD 11 and/or IMD 13 as illustrated and described with respect to FIG. 1), include one or more sensors and sensing circuitry configured to generate a pressure signal, and processing circuitry 60 determines patient parameter values related to blood pressure based on information received by and/or generated from sensors within IMD 15.

Therapy delivery circuitry 64 is configured to generate and deliver electrical therapy to the heart. Therapy delivery circuitry 64 may include one or more pulse generators, capacitors, and/or other components capable of generating and/or storing energy to deliver as pacing therapy, defibrillation therapy, cardioversion therapy, other therapy or a combination of therapies. In some instances, therapy delivery circuitry 64 may include a first set of components configured to provide pacing therapy and a second set of components configured to provide anti-tachyarrhythmia shock therapy. In other instances, therapy delivery circuitry 64 may utilize the same set of components to provide both pacing and anti-tachyarrhythmia shock therapy. In still other instances, therapy delivery circuitry 64 may share some of the pacing and shock therapy components while using other components solely for pacing or shock delivery.

Therapy delivery circuitry 64 may include charging circuitry, one or more charge storage devices, such as one or more capacitors, and switching circuitry that controls when the capacitor(s) are discharged to electrodes 65 and the widths of pulses. Charging of capacitors to a programmed pulse amplitude and discharging of the capacitors for a programmed pulse width may be performed by therapy delivery circuitry 64 according to control signals received from processing circuitry 60, which are provided by processing circuitry 60 according to parameters stored in memory 61. Processing circuitry 60 controls therapy delivery circuitry 64 to deliver the generated therapy to the heart via one or more combinations of electrodes 65, e.g., according to parameters stored in memory 61. Therapy delivery circuitry 64 may include switch circuitry to select which of the available electrodes 65 are used to deliver the therapy, e.g., as controlled by processing circuitry 60.

Communication circuitry 68 includes any suitable hardware, firmware, software or any combination thereof for communicating with another device, such as an external device(s) 20, or another IMD or sensors, such as IMD 1 and/or IMD 13 as shown in FIG. 1. Under the control of processing circuitry 60 as shown in FIG. 3, communication circuitry 68 may receive downlink telemetry from and send uplink telemetry to external device(s) 20 or another device with the aid of antenna 72 which may be arranged according to any of the example antennas described herein, or any equivalents thereof. In some examples, communication circuitry 68 may communicate with a local external device, for example through one or more of external device (20) (FIG. 1), and processing circuitry 60 may communicate with a networked computing device via the local external device and a computer network, such as the Medtronic® CareLink® Network developed by Medtronic, plc, of Dublin, Ireland.

A clinician or other user may retrieve data from IMD 15 using external device(s) 20 (FIG. 1), or another local or networked computing device configured to communicate with processing circuitry 60 via communication circuitry 68. The clinician may also program parameters of IMD 15 using external device(s) 20 (FIG. 1) or another local or networked computing devices.

In various examples, processing circuitry 60 is configured to receive signals from sensing circuitry 62, sensors 66, and or sensor signal provided by sensors external to IMD 15, to process these sensor signals to generate one or more input parameters based either directly on or derived from the sensor signals. The input parameters are associated with current value(s) for one or more physiological parameters associated with a patient, such as patient 12. The physiological parameters associated with the input parameters may include activity counts, respiration rates, breathing rates, movements, postures, and changes in postures associated with a patient. The current values associated with these input parameters can be values measured directly from the input parameters, or derived for these input parameters. For example, a value of a heartrate, measured for example in heartbeats per minute or cardiac cycle length, may be determined as the current value (e.g., the most recent value) for the input parameter associated with the heart rate of the patient measured over some predefined time period. Similarly, a value of a breathing rate, measured for example in breaths per minute or breathing cycle length, may be determined as the current value (e.g., the most recent value) for the input parameter associated with the breathing rate of the patient as measured over some predefined time period.

Similarly, current values can be determined for other input parameters, such as activity count (e.g., based on movement of the patient measured for example in steps taken by the patient per minute), body temperature, and for example a current value for a posture of the patient (e.g., lying down, standing, sitting). A current value of a physiological parameter may be, in some examples, a mean or median of measured values over a period of time. These sensed and determined parameters associated with the patient may be used to control the therapy delivery circuitry 64 in providing electrical stimulation therapy, for example pacing and/or shock therapy, to the patient.

FIG. 4A is an exploded view 100 of an example IMD 15 according to various examples described in this disclosure. As shown in FIG. 4A, IMD 15 includes a power source 48 at least partially enclosed within a case 30 of the IMD. As shown in FIG. 4A, the power source 48 and case 30 may each have an upright cylindrical shape having longitudinal axis 102. Power source 48 and case 30 may also have a circular cross-sectional shape in the planes perpendicular to longitudinal axis 102, for example a plane including axis 104, 106, and planes parallel to the planes including axis 104, 106 that intersect power source 48 and case 30 in cross-section. The power source 48 includes a power connector 49 extending from a top surface 47 of the power source. IMD 15 includes an antenna 50 having an upright circular cylindrical shape and a central axis corresponding with a longitudinal axis 102 of IMD 15, the antenna comprising an electrical conductor forming an antenna winding that is wound around a passageway 52. Passageway 52 is arranged to provide a through-opening that passes through the antenna winding from a bottom surface 53 of antenna 50 to a top surface 54 of the antenna, the passageway 52 having a circular cylindrical shape with a central axis along longitudinal axis 102 of IMD 15. Antenna 50 and passageway 52 may each have an upright cylindrical shape with circular cross-sections, wherein the diameter of the circular cross-section of the antenna 50 is less than the inside diameter of the side walls of case 30, and wherein a diameter of the circular cross-section of passageway 52 is less than the diameter of the antenna 50. While the shapes of these devices have generally been described as having a circular cross-sectional shape, other shaped in cross-section, such as elliptical and oval shapes, are contemplated for one or more of these devices.

IMD 15 further includes electronic circuitry 56, such as electronic circuitry 70 (FIG. 2) that is configured to received electrical power from power source 48, and to perform any of the functions and to provide the features ascribed to IMD 15 when powered by electrical power source 48. As shown in FIG. 4A, electronic circuitry 56 may be provided as a puck that may be at least partially enclosed in cap 38, wherein cap 38 is mechanically coupled to fixation mechanisms 42, 46. Cap 38 may also be mechanically coupled to tip electrode 40, wherein tip electrode 40 is electrically coupled to electronic circuitry 56, and is exposed to the external surface of cap 38 so that the tip electrode may be brought into contact with tissue of a patient when IMD 15 is implanted within the patient. In various examples, tip electrode 40 is a disc shape, having a center point positioned along longitudinal axis 102 of the IMD 15. In various examples, cap 38 is configured to engage the top edge of case 30 to form a hermetically sealed enclosure for power source 48, antenna 50, and electronic circuitry 56. When cap 38 is assembled to case 30, the passageway 52 of antenna 50 has received power connector 49 within the passageway 52, and power connector 49 extending through the passageway 52 so that a contact tip 45 of power connector 49 is in physical contact with an electrical contact area on the bottom surface of the puck including the electronic circuitry 56. Cap 38 is shown in FIG. 4A as including two fixation mechanisms 42, 44 for the purpose of clarity. Examples of IMD 15 may include a two fixation members, or some other number of fixation members, for example three or four fixation members.

In some examples, a shape of the sides of power connector 49 is configured to match a shape, but with a smaller overall dimension, relative to the shape and overall inside dimension in cross-section of passageway 52. For example, a cross-section (e.g., perpendicular to longitudinal axis 102) of power connector 49 may comprise a circular shape having a diameter that is smaller than a diameter of a circular cross-sectional shape of passageway 52, the shape and diameter of passageway 52 maintained throughout the length of the passageway along longitudinal axis 102. As such, the power connector 49 may be advanced through passageway 52 to extend from the power source 48 to the electrical contact area of the puck that comprises electronic circuitry 56 without mechanical interference. The physical contact between contact tip 45 of power connector 49 and the electrical contact area of the puck provides an electrical connection between a first electrical terminal of power source 48 coupled to power connector 49 and the electronic circuitry 56 included in the puck. As shown in FIG. 4A, contact tip 45 is illustratively represented as having a blunt or flat shape. However, in various examples contact tip 45 may be extended to have a rounded or pointed shaped tip. The shape of contact tip 45 may be made to provide lead-in to help guide contact tip 45 and power connection 49 into passageway 52 of antenna 50 during an assembly process used to position power connection 49 at least partially within passageway 52. The coupling of cap 38 and case 30 in some examples provides the return electrical path for electrical energy provided by power source 48 to the electronic circuitry 56 in the puck.

The fit between the sides of power connector 49 and passageway 52 may be kept to a minimum, for example comprising a flush or press fit between the power connector 49 and the walls of the passageway 52, in order to minimize any space not utilized by the power connector 49 or the antenna windings of antenna 50 surrounding the side of passageway 52. Minimization of any unused space between power connector 49 and antenna 50 within passageway 52 may contribute to the ability of this arrangement of the IMD to provide a more compact, and in some examples, a smaller implantable device.

FIG. 4B is a cutaway view 110 of an example of IMD 15 according to various examples described in this disclosure. As shown in FIG. 4B, IMD 15 includes power source 48, antenna 50 and circuit package 58. Power source 48 may be at least partially enclosed within a case 30 of the IMD. Antenna 50 may be arranged adjacent to a top surface 47 of power source 48, antenna 50 including a passageway 52 passing through antenna 50 along a longitudinal axis of the antenna. Power connector 49 is electrically coupled to a first electrical potential of power source 48, and extends from power source 48 into passageway 52. As shown in FIG. 4B, power connector 49 includes a resilient mechanism 112 included within power connector 49, the resilient member configured to urge a contact tip 45 of power connector 49 in a direction along the longitudinal axis 102, through passageway 52, and toward electrical contact area 118 located on the bottom surface 57 of circuit package 58.

In various examples, electrical contact area 118 extends down into passageway 52, and makes electrical contact with power connection 49 within the passageway 52. In some examples where contact is made between electrical contact area 118 and power connection 49 within passageway 52, power connection including contact tip 45 do not extent beyond the passageway 52 in the direction toward circuit package 58. A structural member 114, engages a top surface of circuit package 58 and cap 38 (cap 38 not fully shown in FIG. 4B for clarity). In various examples, structural member 114 is made of an insulative material, such as a non-conductive plastic, and includes one or more electrical contacts for electrically coupling the electronic circuitry included in circuit package 58 with one or more electrodes of IMD 15. For example, one or more of electrical pads 114 may couple the electronic circuitry including in circuit package 58 to the tip electrode 40, via electrical conductor 116. One or more of electrical pads 114A may electrically couple the electronic circuitry including in circuit package 58 to cap 38, and thus to case 30 and a second terminal (second voltage potential) of power source 48.

FIG. 4C is another cutaway view 120 of an example of IMD 15 according to various examples described in this disclosure. A more close-up view of the power connector 49 extending through passageway 52 of antenna 50 is provided in view 120. As shown in FIG. 4C, the resilient mechanism 112 includes a resilient member 113, for example a spring, contained within resilient mechanism 112 and configured to exert a force on a portion of power connector 49 that urges contact tip 45 of the power connection toward the electrical contact area 118, in the direction generally indicated by arrow 115. Contact tip 45 is shown in FIG. 4C as being at some distance from electrical contact area 118 for illustration purposes. When final assembly of IMD 15 has been completed, resilient mechanism 112 and resilient member 113 are configured to have urged the contact tip 45 in the direction of arrow 115 so that the contact tip is brought into physical contact with the electrical contact area 118, thus electrically coupling the terminal of power source 48 that is couple to power connector 49 with the electrical circuitry including in circuit package 58.

As shown in FIG. 4C, IMD 15 may include a coil form 122 that boarders one or more portions of antenna 50. Coil form 122 in some examples is formed of a non-conductive material, such as a non-conductive plastic, and may be formed to contact and/or support portions of antenna 50. In some examples, portions of coil form 122 may at least partially or may wholly surround the outside edges of the windings of the electrical conductor forming antenna 50. In some examples, portions of coil form 122 may at least partially or may wholly cover the bottom and/or the top surfaces of the winding of the electrical conductor forming antenna 50. In various examples, portion of coil form 122 may at least partially extend into and/or may at least partially form a lining of passageway 52. Coil form 122 may be used to provide a shape and support for the electrical conductor at the time the electrical conductor is being formed into the windings of antenna 50. In other examples, the windings of the electrical conductor forming antenna 50 are formed without the use or aid of coil form 122, and antenna 50 is then installed in some position in contact with coil form 122 before final assembly of IMD 15. Coil form 122 may be provided on some examples to protect the windings of antenna 50 during and/or after the final assembly of IMD 15. In various examples, portions of coil form 122 are used to mechanically secure the antenna 50 to the circuit package 58, for example prior to final assembly of the IMD. In various examples of IMD 15, no coil form is provided as part of the final components assembled as IMD 15.

Figure 4D:
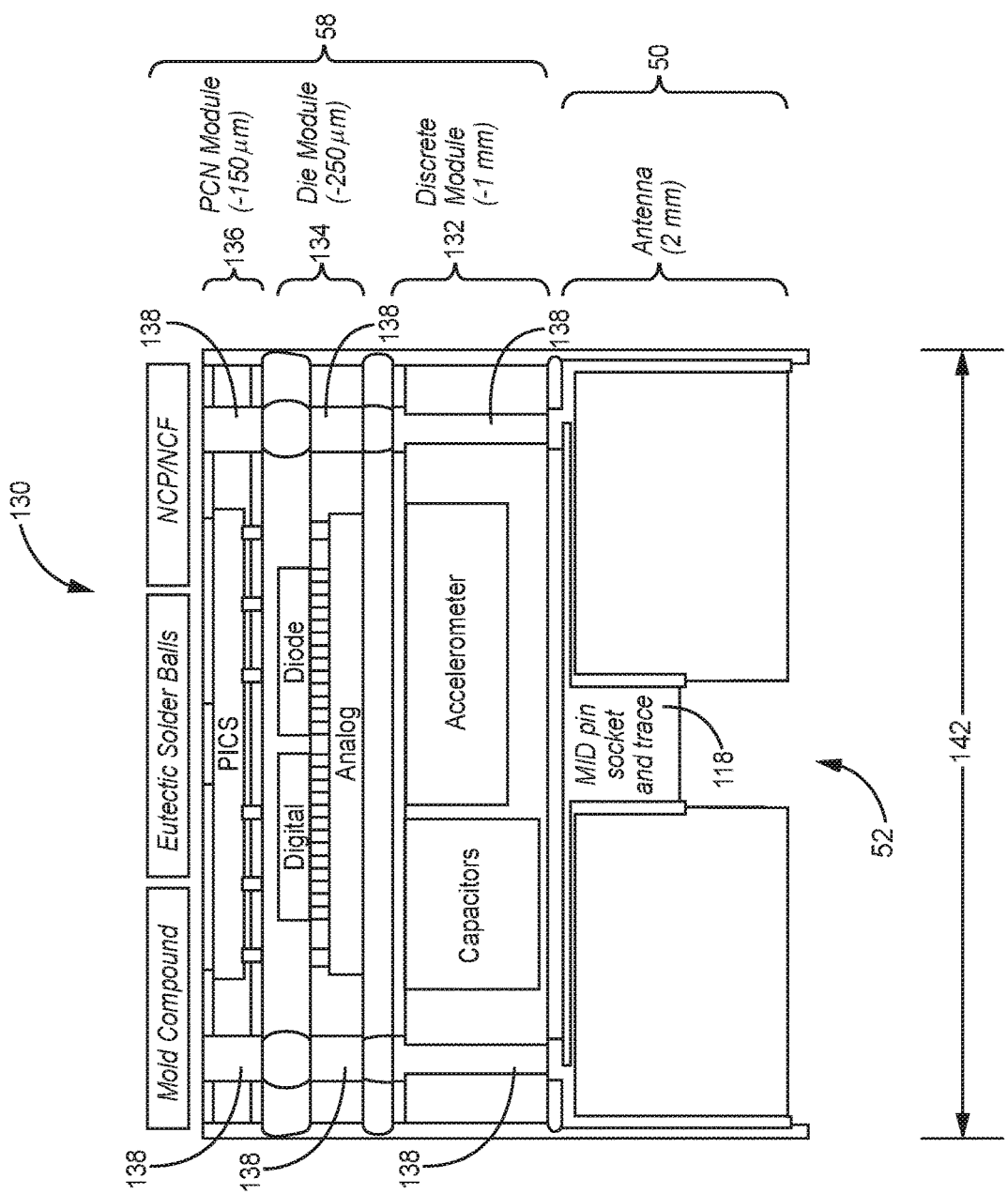
FIG. 4D is a conceptual diagram illustrating an example of portions of an IMD according to various examples described in this disclosure.

FIG. 4D is a conceptual diagram 130 illustrating an example of portions of IMD 15 according to various examples described in this disclosure. As shown in FIG. 4D. IMD 15 includes circuit package 58 and an antenna 50. Circuit package 58 include electronic circuitry 56, which may include devices providing the electronic circuitry 70 as illustrated and described with respect to FIG. 3. As shown in FIG. 4D, electronic circuitry of circuit package 58 may include a Passive Component Network (PCN) layer 136, a die module layer 134, and discrete module layer 132. Die module layer 134 may be electrically coupled to the electrical conductor forming the windings of antenna 50 in order to couple antenna 50 to communication circuitry incorporated into the die module layer. In various examples, each of the PCN module layer 136, the die module layer 134, and the discrete module layer 132 are coupled to the power supply (not shown in FIG. 4D, but for example power source 48 (FIG. 2) or power source 63 (FIG. 3)) providing power to the electronic circuits included within circuit package 58 by one or more power vias 138. In some examples, at least one of power vias 138 is electrically couple to the electrical contact area 118 positioned at the end of passageway 52. As described above, an electrical connector, such as electrical connector 49 (e.g., as shown in FIGS. 2, 4A-4C), is configured to extend through passageway 52 and to contact electrical contact area 118 in order to electrically couple electrical contact area 118 to a first terminal of the power source included within IMD 15.

In various examples, as shown in FIG. 4D, electrical contact area 118 is a pin socket that extends into passageway 52. In various examples, the power connection 49 is not configured to extend through the entirety of the length of passageway 52, but instead is configured to electrically couple with the portion of the pin socket that extends down into passageway 52. The portion of electrical contact area 118 that extends into passageway is electrically coupled, for example through a plated surface, to one or more of the vias 138 to allow electrical power provided at power connection 49 to be coupled to the electronic circuitry in circuit package 58. As such, when IMD 15 is fully assembled, electrical power from the first terminal of the power source included within the IMD may be electrically coupled to the electronic circuitry 56 of circuit package 58. In various examples, at least one of vias 138 that is not directly coupled to the electrical contact area 118 may be coupled to the second terminal of the power source provided within IMD 15, thus providing a return path for the current received from the power source by the electronic circuitry including in circuit package 58.

In various examples, a Passive Component Network (PCN) layer 136 including the processing circuitry, and in some examples the memory, used to provide the processing required to performed the functions and to provide the features ascribed to IMD 15 throughout this disclosure, and any equivalents thereof. In various examples, the discrete module layer 136 may include devices provide using Surface Mount Technology (SMT), and may include devices such as accelerometers used to determine position and or motions occurring with respect to IMD 15 when IMD 15 is assembled and operational. Discrete module layer 132 may include one or more capacitors that are used to store a charge that may be applied to one or more electrodes of the IMD when the IMD is providing therapy to a patient. For example, capacitors in the discrete module layer 132 may store a charge that can then be applied to the tip electrode 40 (not shown in FIG. 4D) of the IMD for providing pacing and/or defibrillation therapy, or some other form of electrical stimulation to the patient. In various examples, electrode connections provide conductive pads that may be electrically coupled to the electrodes and/or in the end cap and/or case of IMD 15 to provide the additional electrical paths required for performing the functions and providing the features ascribed to IMD 15 throughout this disclosure, and any equivalents thereof.

Various dimension of the circuit package 58 and the antenna 50 are provide in FIG. 4D. These dimensions are intended to be illustrative, and are not intended to be limiting with respect to other dimensions and/or ranges of dimensions that may exist for the portions of IMD 15 illustrated in FIG. 4D. As shown in FIG. 4D, a height dimension for antenna 50 may have a value of approximately 2 millimeters (mm). A height dimension for the discrete module layer 132 may have a value of about 1 mm, a height dimension for the die module layer 134 may have a value of about 0.250 mm, and a height dimension for the PCN module layer 136 may have a value of about 0.150 mm. In various examples, each of the layers of circuit package 58 and antenna 50 may have a cross sectional dimension 142 having a value in a range of 0.3 mm to 5 mm. Dimension 142 in some examples represents a diameter for a circular cross-section of each of the layers of circuit package 58 and antenna 50, wherein this circular cross-sectional dimension has a value that is smaller than an inside cross sectional dimension of the case of IMD 15, allowing the portions of IMD 15 as illustrated in FIG. 4D to be inserted into at least some portion of the case, and hermitically within the case upon final assembly of IMD 15. Dimension 142 may have a value in a range of 8 to 28 French (Fr) in various examples of IMD 15, wherein 1 Fr=1 millimeter·π (Pi). In various examples, dimension 142 is approximately 14 Fr.

Figure 4E:
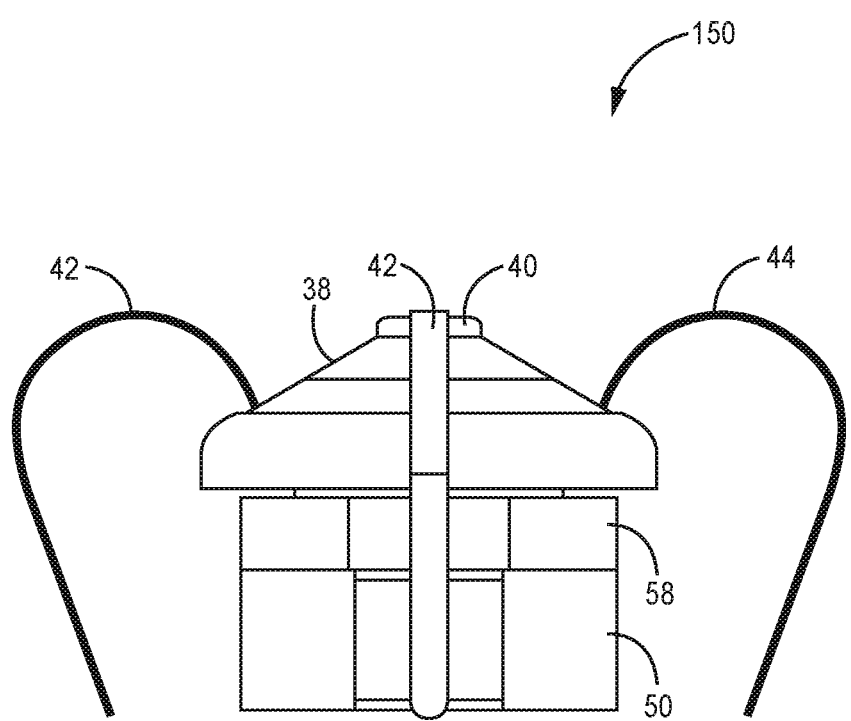
FIG. 4E is a diagram illustrating an example portion of an IMD according to various examples described in this disclosure.

FIG. 4E is a diagram 150 of an example of portions of IMD 15 according to various examples described in this disclosure. As shown in FIG. 4E, an antenna 50 is mechanically coupled adjacent to a bottom surface of a circuit package 58, wherein circuit package 58 include the electronic circuitry, such as electronic circuitry 70 illustrated and described with respect to FIG. 3. The assembly including antenna 50 and circuit package 58 as shown in FIG. 4E is mechanically coupled to cap 38, wherein cap 38 includes a plurality of fixation mechanisms 42, 44, extending from the exterior surface of the cap. Cap 38 also includes electrode 40 positioned on a center portion of the cap. In various examples, the assembly illustrated in diagram 150 may be joined together with a case and a power source (such as case 30 and power source 48 illustrated and described for example with respect to FIGS. 2 and 4A-4C), so that a power connection extending from the power source extends up into and at least partially through a passageway provide along the longitudinal axis of antenna 50, as described throughout this disclosure. When the assembly as shown in diagram 150 is joined together with the case and power source, the case and cap may be sealed, for example by welding or by an adhesive compound, to form a hermitically sealed housing enclosing the power source, the antenna, and the puck. After joining the case and the power source with the assembly shown in diagram 150, the power connection extending through the passageway of antenna 50 may provide at least one electrical connection between the electronic circuitry included in the puck and the power source enclosed within the case, with a bottom surface of the antenna located adjacent to a top side of the power source.

Figure 4F:
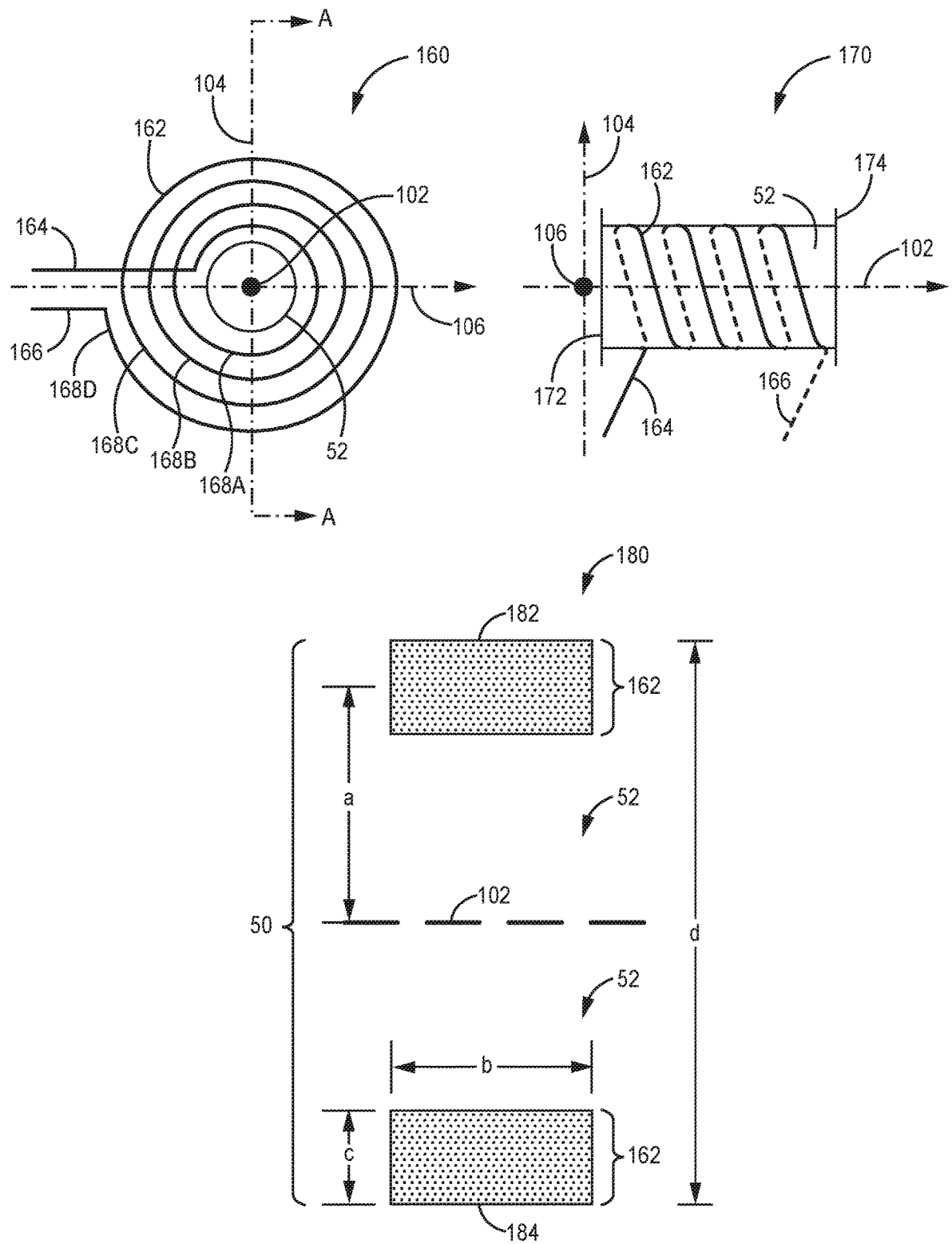
FIG. 4F illustrates conceptual diagrams of examples of winding techniques and parameters for an antenna according to various examples described in this disclosure.

FIG. 4F illustrates conceptual diagrams 160, 170, and 180 of examples of winding techniques and parameters for an antenna 50 according to various examples described in this disclosure. The conceptual diagrams 160, 170, and 180 as shown in FIG. 4F are meant to be illustrative of concepts associated with the windings of the electrical conductor(s) that may be used to form examples of antenna, and are not meant to provide scale or to provide dimensionally proper information unless specifically stated as providing these in the description below. As illustrated in diagram 160, and electrical conductor 162 may be wound around passageway 52, in a substantially circular shape, and comprising a series of layers 168A, 168B, 168C, and 168D. The view of the windings illustrated in diagram 160 is such that the longitudinal axis 102 of the antenna extends into and out of the drawing, away from the viewer and toward the viewer, respectively, viewing the drawing as illustrated in diagram 160. Each of axis 104, 106 are perpendicular to the longitudinal axis 102, and are perpendicular to each other. In general, a dimensional value of the diameter of passageway 52 along axis 104 is substantially equal the dimensional value of the diameter of passageway 52 along axis 106.

Each of layers 168A, 168B, 168C and 168D surrounds at least a portion of, or for some layers all of the passageway 52, and are electrically coupled to one another by virtue of being formed from a single electrical conductor 162, but are insulated from one another throughout the skin of the electrical conductor 162 by use of an insulative coating, such as lacquer, coating the exterior surface of electrical conductor along the entirety of the electrical conductor the forms the circular windings of the antenna. Electrical conductor 162 is not limited to any particular type of electrical conductor, and in some examples is formed of a metallic conductor, such as copper. Electrical conductor 162 may be formed as a wire, and may have a circular cross-section along the length of the electrical conductor. In some examples, electrical conductor 162 is formed using Litz wire. In some examples, electrical conductor 162 is formed using copper magnetic wire. Electrical conductor 162 is not limited to being formed of a conductor having a particular cross-sectional area or a particular having a particular gauge. Electrical conductor 162 may be formed using 45 AWG (American Wire Gauge) wire. Electrical conductor 162 may be formed using 50 AWG wire.

Each layer of electrical conductor 162 may comprise one or more windings surrounding passageway 52 and having a substantially same diameter or distance from the outside diameter of the passageway throughout the layer, and a diameter or distance that is different from the diameter or distance of the other layers of the winding relative to the outside diameter of passageway 52. For example layer 168A may comprise one or more windings of electrical conductor 162 that at least partially surround or completely surround the side of passageway 52, and are positioned at a first distance from the center point of passageway 52 indicated by longitudinal axis 102. At least one winding of the first layer 168A may not completely surround the side of passageway 52 by virtue of being coupled to a first lead 164 that provides a first connection point to the winding formed by electrical conductor 162. Additional winding of electrical conductor 162 included in layer 168A may completely surround the side of passageway 52.

A second layer 168B of windings of electrical conductor 162 may comprise one or more winding that each completely surround the side of passageway 52, and are formed on top of the first layer 168A and on the side of first layer 168A that faces away from the passageway. As such, the windings of electrical conductor 162 forming the second layer 168B and are positioned at a second distance from the center point of passageway 52 that is greater than the first distance of layer 168A relative to the center point of passageway 52. In some examples, the difference between the first distance and the second distance is a thickness of the electrical conductor 162 itself.

In a similar manner, the third layer 168C of windings will be formed on an outer surface of the second layer 168B and having each winding completely surrounding the side of passageway 52 at third distance from the center point of the passageway, the third distance being a larger distance from the center point relative to the first distance of first layer 168A and to the second distance relative to second layer 168B.

Layer 168D represents the outermost layer of windings of electrical conductor 162, and may be formed on the top surface of the third layer 168C. Each of the windings of layer 168D may partially or completely surround the side of passageway 52. At least one winding of the layer 168D may not completely surround the side of passageway 52 by virtue of being coupled to a second lead 166 that provides a second connection point to the windings formed by electrical conductor 162. Additional windings of electrical conductor 162 included in layer 168D may completely surround the side of passageway 52.

Because the windings of layer 168D are formed on the outer side of the winding forming layer 168C, the winding of electrical conductor 162 forming the outermost layer 168D are positioned at a fourth distance from the center point of passageway 52 that is great than the first, second, and third distances of layer 168A, 168B, and 168C, respectively, relative to the center point of passageway 52. The number of windings per layer, and the number of layers as depicted and/or described with respect to diagram 160 are illustrative of the physical relationship of the windings and the layers, and re not intended to represent the actual numbers of windings per layer, or the actual number of layers, that may be included in given example of an antenna. More details regarding the number of windings and the arrangement of the windings are illustrated and described below with respect to diagrams 170 and 180.

Diagram 170 illustrates another conceptual diagram of the winding of electrical conductor 162 to form antenna 50. The view of the windings illustrated in diagram 170 is such that the longitudinal axis 102 of the antenna extends from right to left across the drawing. Axis 104 remains in a vertical orientation in diagram 170. Axis 106 in diagram 170 is oriented into and out of the drawing, away from the viewer and toward the viewer, respectively, when viewing the drawing as illustrated in diagram 170. Each of axis 104, 106 is perpendicular to the longitudinal axis 102, and are perpendicular to each other.

A single layer of windings, for example first layer 168A, is illustratively represented in diagram 170. The electrical conductor 162 in diagram 170 is coupled to first lead 164 near a first side 172 of the antenna. Electrical conductor 162 extends from first lead 164 around a backside of passageway 52, and across the front side of passageway 52, forming a plurality of windings extending adjacent to one another and from the first side 172 toward a second side 174 of the antenna. Each of the windings illustrated in diagram 170 would be positioned at approximately as same distance from the center point, illustrated by the position of longitudinal axis 102, of passageway 52. The spacing between the individual winding as shown in diagram 170 is exaggerated for illustration purposes, for example to show the portions of the winding extending across the backside of passageway 52. In actual practice, the individual windings of the layer of windings as shown in diagram 170 may contact the adjacent winding on one or on both sides of the winding, forming a substantially solid layer of the electrical conductor extending from first side 172 to second side 174 of the antenna.

In various examples, additional layers of windings of electrical conductor 162 would be wound over the layer of winding illustrated in diagram 170, for example as layers 168B, 168C, and 168D shown and described with respect to diagram 160. Once the additional windings have been provided over the layer illustrated in diagram 170, a final winding would exit away from passageway 52 to form the second lead 166, as illustrated by the dashed line in diagram 170.

In some examples, the passageway 52, first side 172, and second side 174 shown in diagram 170 may comprise a coil form, (such as coil form 119, 122 illustrated and described with respect to FIGS. 4B, 4C, respectively), that physically supports and provides boundaries for the windings formed using electrical conductor 162. For example, the portion of the coil form may form the cylindrical shape used to support the individual windings of the electrical conductor 162 surrounding the side of passageway 52. In addition, first end 172 and second end 174 may provide support and limit the extent of the windings of the electrical conductor in order to provide a first and second flat side, for the antenna. First end 172 of the coil form may provide a flat side of the antenna that may be located adjacent to the top side of the power source, and second side 174 of the coil form may provide a flat side of the antenna that may be located adjacent to a bottom surface of the puck that includes the electronic circuitry when assembled into an IMD. In various examples, the shape of the windings of the antenna is formed without the use of a coil form, or may be wound with the aid of some type of coil form that does not ultimate become a part of the IMD when the antenna is installed in the IMD or upon final assembly of the IMD.

Diagram 180 illustrates another conceptual diagram depicting a cutaway view of the winding of electrical conductor 162 as illustrated in diagram 160. As shown in diagram 180, passageway 52 extends along longitudinal axis 102, and extends between an upper portion 182 of the windings of electrical conductor 162 and a lower portion 183 of the winding the electrical conductor 162. As shown in diagram 180, each portion of the windings of electrical conductor 162 in both the upper portion 182 and the lower portion 183 is shown in cross section, for example as a circular cross-section in examples where electrical conductor 162 comprises a circular shaped conductor, for example a round wire.

Various dimension and other parameters of the windings used to form example antennas are described below with respect to diagram 180. Because antenna may be axially symmetrical relative to longitudinal axis 102, a dimension or dimensions described with respect to the upper portion 182 may be equally applicable to a corresponding dimension or dimensions for the lower portion 183, and a dimension or dimensions described with respect to the lower portion 183 may be equally applicable to the corresponding dimension or dimensions of the upper portion 182. Some of these dimensions and other parameters are associated with what is generally referred to a "Brooks coil" or correspond to dimensions associated with a Brooks coil and/or a Brooks approximation. In general, a Brooks coil comprises a circular coil of an electrical conductor having a rectangular cross section for the upper and lower portions, and may provide a maximum inductance for a given length of the electrical conductor used to form the coil.

As shown in diagram 180, antenna 50 include a radius ("a") extending from the center point to a mid-point of the thickness dimension ("c") of the upper portion 182 individually and for the lower portion 183 individually, dimension "a" measured perpendicular to longitudinal axis 102. A width dimension ("b") of the upper portion 182 and a same width dimensions "b" for the lower portion is the width dimensions measured parallel to longitudinal axis 102. Antennas 50 also includes an overall outer dimension ("d") (e.g., and outside diameter) extending from the outside edge of upper portion 182 to the lower edge of lower portion 183, and extending through longitudinal axis 102.

In some examples, antenna 50 is configured to operate at an operating frequency up to approximately 175 kHz, and may be arranged according to the following dimensions and parameters:

radius ("a")=2.05 millimeters (mm)

thickness $c=2/3 \cdot a=1/367$ mm overall diameter $d=2 \cdot (a+0.5c)=5.467$ mm number of turns included in the windings ("NT")—466 to 550 turns wire with insulation=approximately 2 mil diameter 2 mil=50.8 µm Wire Diameter(45)=44.8 µm Width $b = [(NT/c)/(\text{wire Diameter}(45) + 6 \text{ µm})] \cdot$ (Wire Diameter(45) + 6 µm)

= 0.88 mm for 466 turns to 1.039 mm for 550 turns

Using Copper Magnet Wire (CMW)—45 AWG:

CMW(45)=3.3 ohms/foot

Wire length=$2 \cdot \pi \cdot a \cdot NT$=19.693 to 23.242 feet

Wire resistance(45)=wirelength·CMW(45)=64.986 to 76.7 Ohms

Using Copper Magnet Wire (CMW)—50 AWG:

CMW(50)=10.58 ohms/foot

Wire length=$2 \cdot \pi \cdot a \cdot NT$=19.693 to 23.242 feet

Wire resistance(50)=wirelength·CMW(50)=208.348 to 245.905 Ohms

Assuming Brooks approximation that the circular winding cross section is 2a=3c: Inductance of the antennas is calculated as follows:

$L_{BrooksAnt}(a,N) = 1.353 \cdot \mu_0 \cdot a \cdot N^2$ $L_{BrooksAnt}(a,N=466) = 757$ µH $L_{BrooksAnt}(a,N=550) = 1054$ µH For coil quality factor for examples of antenna 50:

$Qq(WR) = (2 \cdot \pi \cdot f \cdot L_{BrooksAnt}(a,NT))/WR$—wherein $f$=operating frequency $Qp$(wireresistane(45))=12.807 for 466 turns to 15.115 for 550 turns $Qp$(wireresistane(50))=3.994 for 466 turns to 4.715 for 550 turns $Q_{ra} = 1/(50 \text{ kHz}/175 \text{ kHz}) = 3.5$ In various examples of antenna 50, these dimensions and/or one or more of these parameters apply to the construction and/or operating parameters of the antenna used in the IMDs, such as IMD 15, described throughout this disclosure, and any equivalents thereof.

Figure 4G:
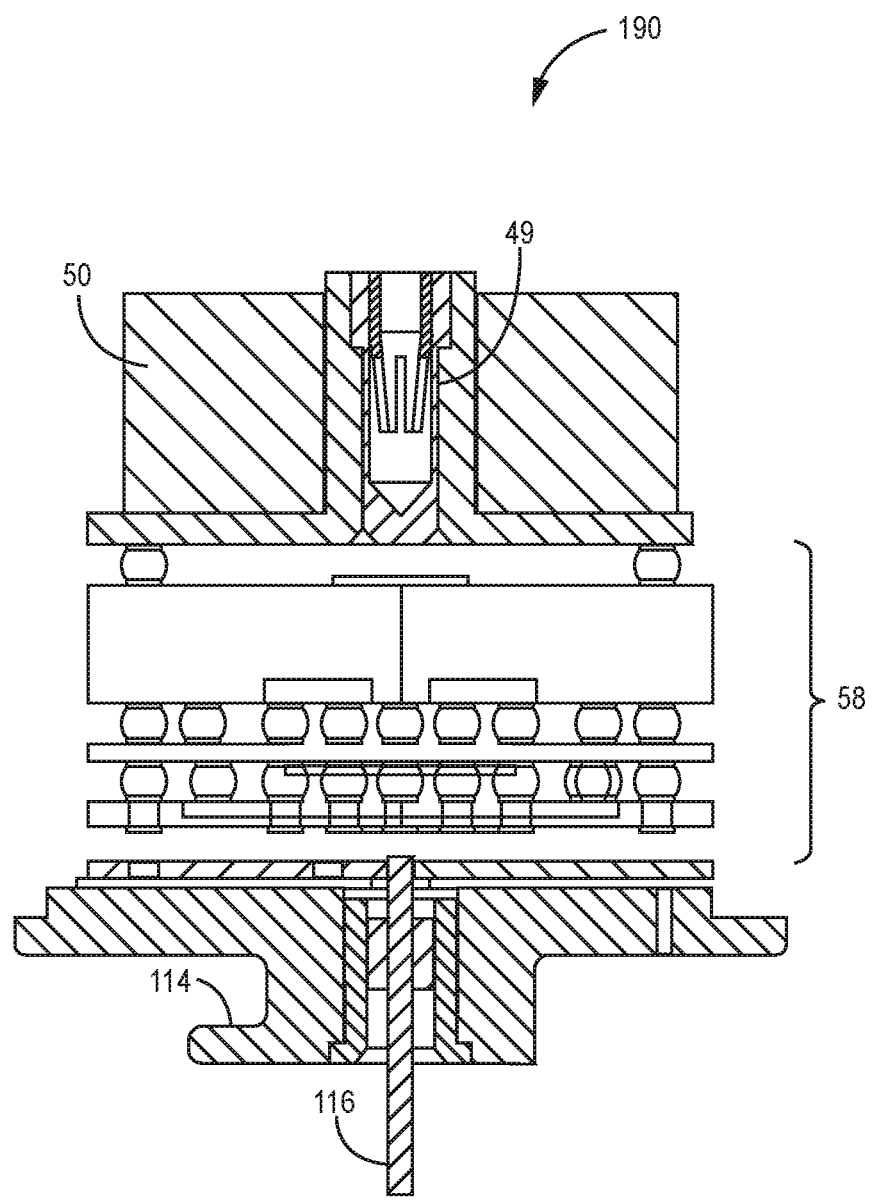
FIG. 4G is another cutaway view of a portion of an example IMD according to various examples described in this disclosure.

FIG. 4G is another cutaway view of a portion 190 of an example IMD 15 according to various examples described in this disclosure. FIG. 4G includes dimensions associated with a portion of an example IMD including antenna 50, power connection 49, circuit package 58, and structural member 114. Dimension shown without brackets are in inches, and dimensions shown within square brackets are in millimeters. Dimensions shown in FIG. 4G are illustrative of dimensions for an example of an IMD according to various examples described in this disclosure, and any equivalents thereof, and are not intended to be limiting with respect to other dimensions and/or ranges of dimensions that may exist for the portions of IMD 15 illustrated in FIG. 4G.

Figure 4H:
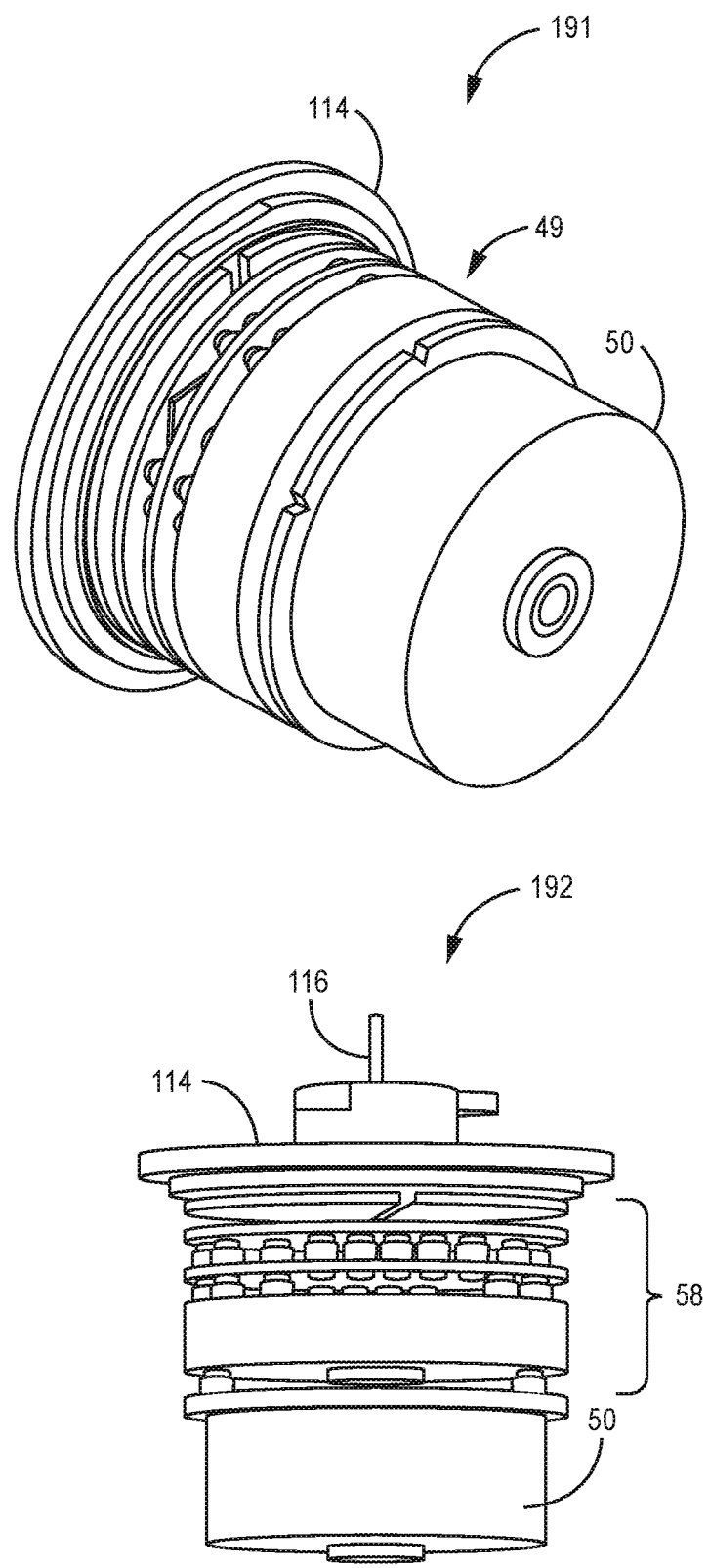
FIG. 4H illustrates conceptual diagrams of perspective views of portions of an example IMD according to various examples described in this disclosure.

FIG. 4H illustrates conceptual diagrams 191 and 192 of perspective views of portions of an example IMD 15 according to various examples described in this disclosure. Reference numbers shown in FIG. 4H correspond to same or similar devices or structures having these same corresponding reference numbers as illustrated and described with respect to FIGS. 4A-4G.

Figure 4I:
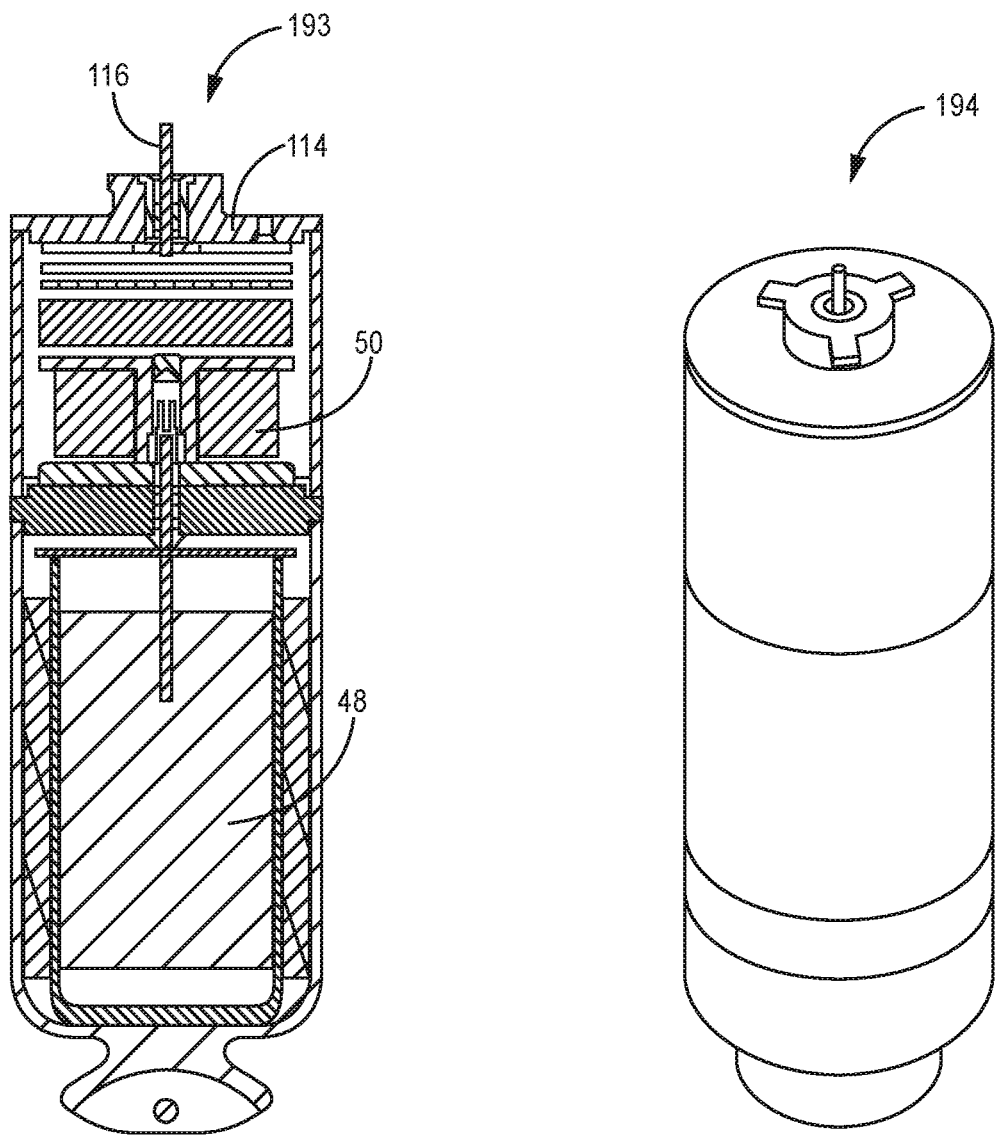
FIG. 4I includes another cutaway view and a conceptual perspective view of a portion of an example IMD according to various examples described in this disclosure.

FIG. 4I includes another cutaway view 193 and a conceptual perspective view 194 of a portion of an example IMD 15 according to various examples described in this disclosure. The dimension shown without brackets in FIG. 4I is in inches. The dimensions shown in FIG. 4I is illustrative of dimensions for an example of an IMD according to various examples described in this disclosure, and any equivalents thereof, and is not intended to be limiting with respect to other dimensions and/or ranges of dimensions that may exist for the portions of IMD 15 illustrated in FIG. 4I.

Figure 4J:
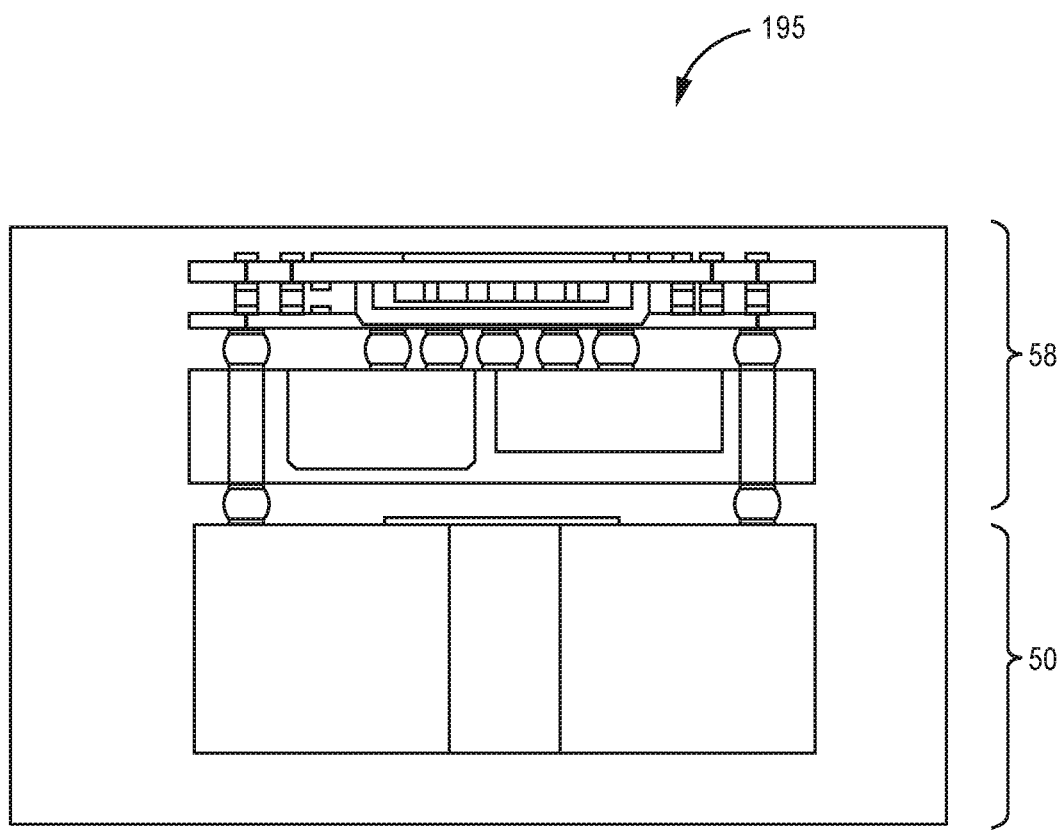
FIG. 4J is a conceptual diagram illustrating an example of portions of an IMD according to various examples described in this disclosure.

FIG. 4J is a conceptual diagram 195 illustrating an example of portions of an IMD according to various examples described in this disclosure. FIG. 4J includes dimensions associated with a portion of an example IMD including antenna 50 and circuit package 58. Dimension shown in FIG. 4J are in micrometers. Dimensions are illustrative of dimensions for an example of an IMD according to various examples described in this disclosure, and any equivalents thereof, and are not intended to be limiting with respect to other dimensions and/or ranges of dimensions that may exist for the portions of IMD 15 illustrated in FIG. 4J.

Figure 5:
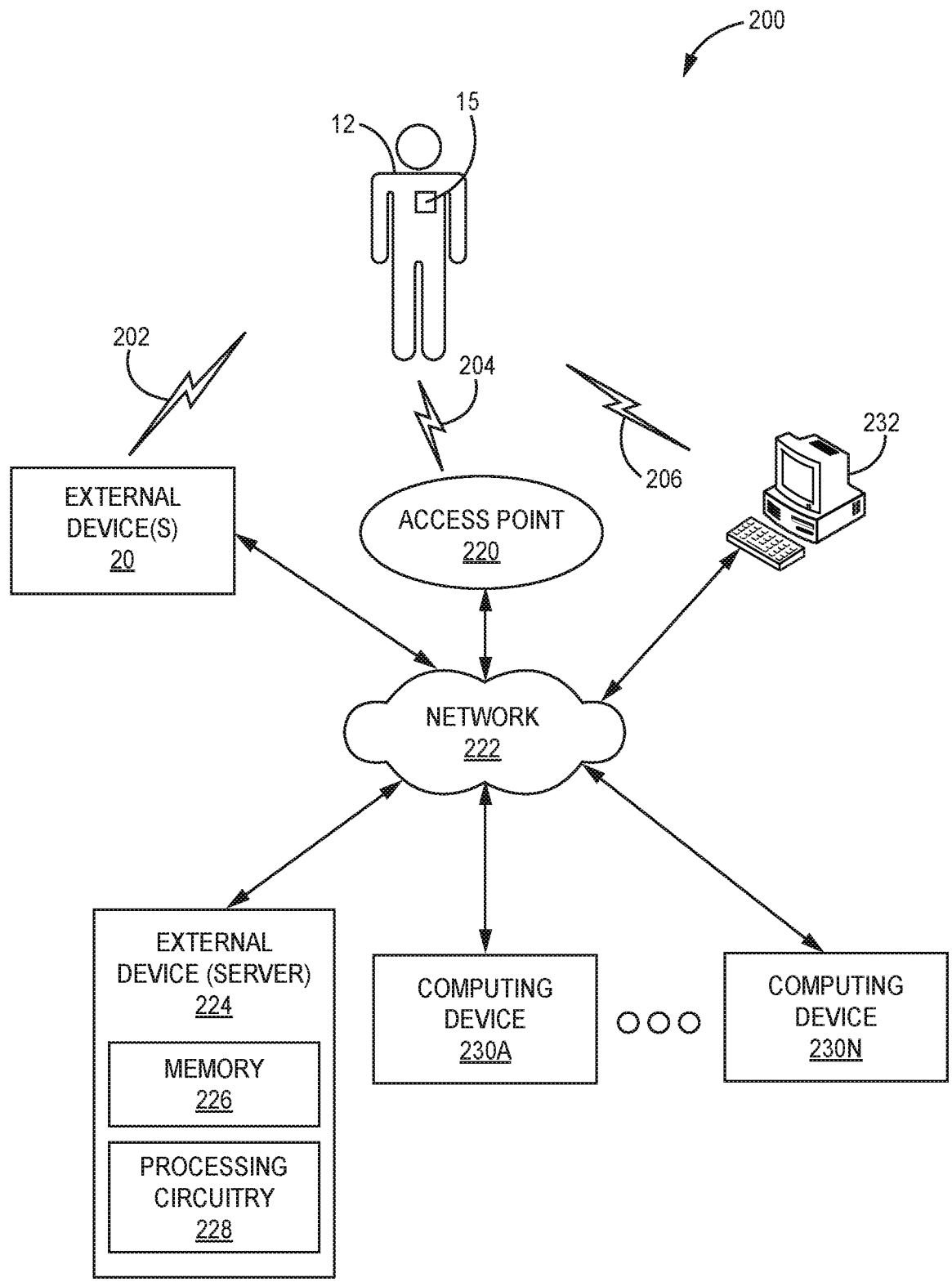
FIG. 5 is a functional block diagram illustrating an example system including an IMD communicatively liked to one or more example external devices according to various examples described in this disclosure.

FIG. 5 is a functional block diagram illustrating an example system 200 including an IMD 15 communicatively liked to one or more example external devices according to various examples described in this disclosure. As shown in FIG. 5 a patient 12 has an IMD 15 implanted within the patient. The location for the implantation of IMD 15 is not limited to any particular part of patient 12, and may be implanted in the heart of patient 12, for examples as illustrated and described with respect to FIG. 1. As shown in FIG. 5. IMD 15 may be communicatively linked to one or more external device(s) 20, access point 220, and/or computing devices 232, via communication links 202, 204, 206, respectively. Communicating links 202, 204, 206 are not limited to any particular types of communication links, or to any particular types of communication formats, and may be any types of links and/or formats that may be used in conjunction with and IMD having an antenna arrangement configured according to the various examples described throughout this disclosure, or any equivalents thereof. In various examples, the antenna included in IMD 15 may be wound and arranged within IMD 15 to maximize the efficiency of the communication links 202, 204, 206, for example with respect to coupling efficiency and effective range between IMD 15 and the devices where communications may still occur between IMD and the other devices illustrated in FIG. 5. The communication links 202, 204, 206 illustratively shown in FIG. 5 may be provided using a same communication format and/or a same communication protocol. For example, one or more of communication links 202 may be provided using Bluetooth Low Energy (BLE) as the communications format. In some examples, one or more of communication links 202, 204, 206 may be provided via the telB communication protocol. Other communication protocols are contemplated for use by communication links 202, 204, 206 for providing communications between IMD 15 and the devices external to the IMD.

System 200 may include external computing devices, such as a server 224 and one or more other computing devices 230A-230N, that are coupled to IMD 15, and external device(s) 20 via a network 222. In this example, IMD 15 may use its communication circuitry 68 to, e.g., at different times and/or in different locations or settings, to communicate with external device(s) 20 via a first wireless connection provided through communication link 202, and to communicate with an access point 220 via a second wireless connection provided through communication link 204. IMD 15 may be coupled to a computer 232 via communication link 206. Computer 232 may include a display and one or more input devices, such as a keyboard and/or a computer mouse, that allow a user to interact with IMD 15, for example to provide programming to IMD 15 related to therapy and/or sensing parameters and instructions for execution by processing circuitry within IMD 15, and/or to access data stored IMD 15, for example regarding current and historical data related to the operations performed by and/or the status of the IMD, and/or parameters sensed by the IMD related to patient 12.

In the example of FIG. 5, computer 232, access point 220, external device(s) 20, server 224, and computing devices 230A-230N are interconnected, and able to communicate with each other, through network 222. Access point 220 may comprise a device that connects to network 222 via any of a variety of connections, such as telephone dial-up, digital subscriber line (DSL), or cable modem connections. In other examples, access point 220 may be coupled to network 222 through different forms of connections, including wired or wireless connections. In some examples, access point 220 may be co-located with the patient. Access point 220 may interrogate IMD 15, e.g., periodically or in response to a command from the patient or network 222, to retrieve physiological measurements and/or other operational or patient data from IMD 15. Access point 220 may provide the retrieved data to server 224 via network 222. In various examples, access point 220 may be any example of transceiver 24 described above.

In some cases, server 224 may be configured to provide a secure storage site for data that has been collected from IMD 15, and/or from external device(s) 20. In some cases, server 224 may assemble data in web pages or other documents for viewing by trained professionals, such as clinicians, via computing devices 230A-230N. The illustrated system of FIG. 5 may be implemented, in some aspects, with general network technology and functionality similar to that provided by the Medtronic® CareLink® Network developed by Medtronic plc, of Dublin, Ireland.

In some examples, one or more of access point 220, server 224, or computing devices 230A-230N may be configured to perform, e.g., may include processing circuitry configured to perform, some or all of the techniques described herein, e.g., with respect to processing circuitry 60 of IMD 15 and external device(s) 20, relating to the communications with IMD 15. In the example of FIG. 5, server 224 includes a memory 226 to store physiological and other data received from IMD 15 and/or external device 20, and processing circuitry 228, which may be configured to provide some or all of the functionality ascribed to processing circuitry 60 of IMD 15 as described herein.

Figure 6:
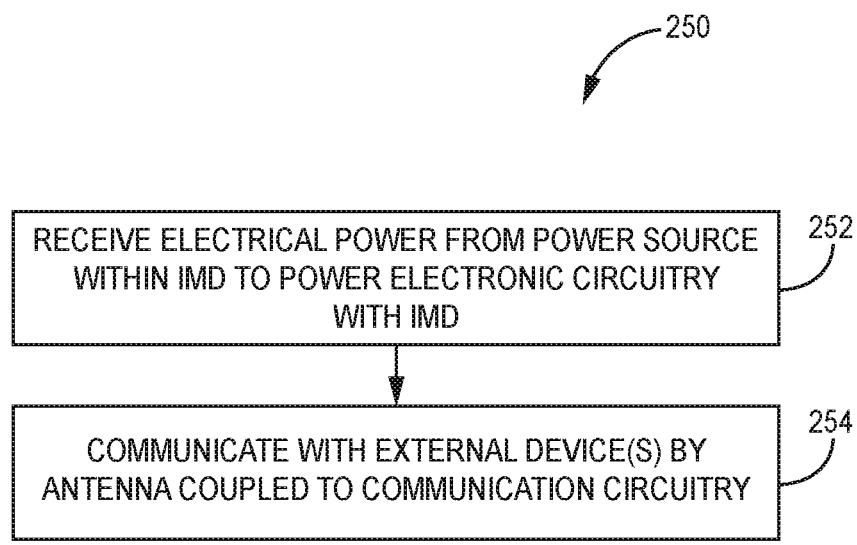
FIG. 6 is a flowchart illustrating a method for operating an implanted medical device according to various examples described in this disclosure.

FIG. 6 illustrates a flowchart illustrating an example method 250 of operating an implanted medical device according to various examples described in this disclosure. Although method 250 describes the operations of an implanted medical device as being performed by IMD 15 as illustrated and described with respect to FIG. 3, method 250 is not limited to being performed by any particular device or devices, and may be performed by any device or devices configured to perform the functions of method 250, including devices and systems as otherwise described herein, and/or any equivalents thereof. According to method 250, IMD 15 receives electrical power, by power connection 74 coupled to power source 63 located within the implanted medical device (block 252). The received electrical power is coupled through power connection 74 to power the electronic circuitry 70 located within the implanted medical device. The power connection 74 is coupled to an electrical terminal of the power source 63 to provide at least one electrical connection between the electrical power provided by power source 63 and to the electronic circuitry 70 of the implantable medical device. In some examples, case 30 provides at least a part of a second connection between second electrical connection 80 between as second terminal 82 of power source 63 and the electronic circuitry 70.

Method 250 also includes, communicating, by an antenna 72 coupled to a communication circuitry 68, with one or more external devices using a signal that is transmitted from the antenna 72 of IMD 15, or that is received by the antenna 72 of IMD 15 (block 254). Communications of method 250 are not limited to any particular type of communication, or to any particular format or protocol for the communications, and may comprise information, data, and/or programming parameters communicated between IMD 15 and one or more external device, using any protocol, described in this disclosure, or any other protocol that would be useful in providing these communication between the IMD 15 and the one or more external devices. In various examples of method 250, antenna 72 comprises an axially symmetrical antenna winding that at least partially surrounds a passageway extending through the antenna winding along a longitudinal axis of the antenna. According to method 250, power connection 74 electrically couples to an electrical terminal of the power source 63 that extends from a top surface of the power source into the passageway on a first side of the antenna 72, and forms an electrical connection with the electronic circuitry 70, including the communication circuitry 68, located on a second side of the antenna 72 opposite the first side of the antenna.

Figure 7:
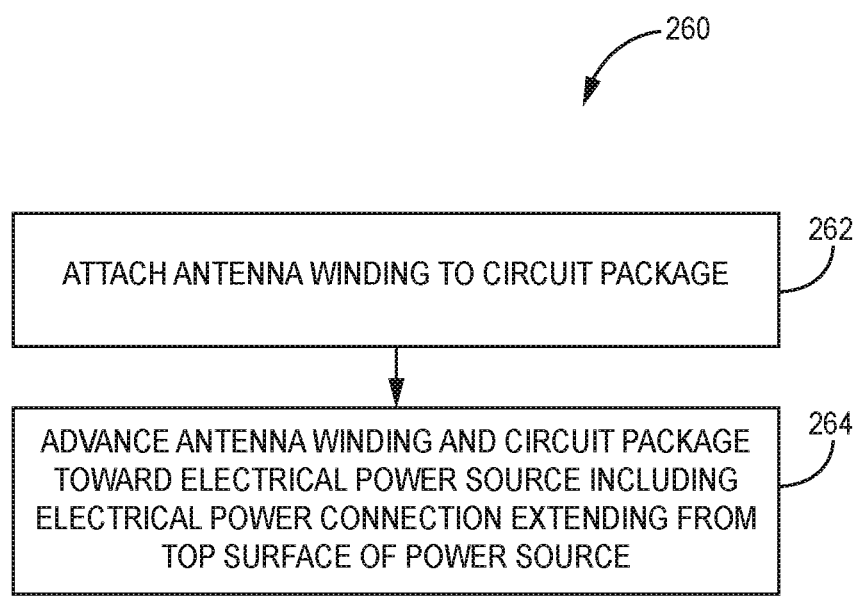
FIG. 7 is a flowchart illustrating a method assembling and implanted medical device according to various examples described in this disclosure.

FIG. 7 illustrates a flowchart illustrating an example method 260 for assembling an implanted medical device according to various examples described in this disclosure. Although method 260 is described the operations of an implanted medical device as being performed by IMD 15 as illustrated and described with respect to FIGS. 4A-4F, method 260 is not limited to being performed based on the particular devices referred to as comprising IMD 15 as illustrated and described with respect to FIGS. 4A-4F, and may be assembled to include an antenna as described herein, and/or any equivalents thereof. According to method 260, assembly of an IMD 15 includes attaching an antenna winding 50 to a circuit package 58 including electronic circuitry 56 (block 262). Method 260 includes assembling the antenna winding comprising a wound electrical conductor having a passageway 52 extending through the antenna winding along a longitudinal axis 102 of the antenna. Assembling the antenna winding 50 to the circuit package 56 in some examples of method 260 includes positioning a top surface 54 of the antenna winding adjacent to a bottom surface 57 of the circuit package 56 so that an electrical contact area 118 is located on the bottom surface 57 of circuit package 58 and aligns with passageway 52 of the antenna winding.

Method 260 further includes advancing the antenna winding 50 and the circuit package 58 toward an electrical power source 48 including an electrical power connection 49 extending from a top surface 47 of the electrical power source so that the electrical power connection advances into the passageway of the antenna winding to form an electrical coupling with the electronic circuitry 56 (block 264). In method 260, advancing the antenna winding toward the electrical power source includes advancing a bottom surface 53 of the antenna toward the top surface 47 of the electrical power source. In some examples, bottom surface 53 of the antenna is advanced to place the bottom surface 53 adjacent to top surface 47 of power source 48. In various examples of method 260, forming the electrical coupling between the electrical power connection and the electronic circuitry 56 of circuitry package 58 includes advancing power connection 49 through passageway 52 toward the top surface 54 of the antenna 50 to bring a contact tip 45 of the power connection into contact with the electrical contact area 118 located on the bottom surface 57 and aligned with passageway 52. As shown in FIG. 4A, contact tip 45 is illustratively represented as having a blunt or flat shape. However, in various examples contact tip 45 may be extended to have a rounded or pointed shaped tip. The shape of contact tip 45 may be made to provide lead-in to help guide and power prove 49 into passageway 52 of antenna 50 during an assembly process used to position power probe 49 at least partially within passageway 52.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like that is tangible. The computer-readable storage media may be referred to as non-transitory. A server, client computing device, or any other computing device may also contain a more portable removable memory type to enable easy data transfer or offline data analysis. The instructions may be executed to support one or more aspects of the functionality described in this disclosure.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various aspects of this disclosure have been described. These and other aspects are within the scope of the following claims.

What is claimed is:

1. An implantable medical device comprising:
   a power source configured to provide electrical power to the implantable medical device;
   an antenna comprising an axially symmetrical antenna winding that at least partially surrounds a passageway extending through the antenna winding along a longitudinal axis of the antenna; and
   a power connection electrically coupled to an electrical terminal of the power source, the power connection extending from a top surface of the power source into the passageway on a first side of the antenna and forming an electrical connection with electronic circuitry located on a second side of the antenna opposite the first side of the antenna, wherein the antenna is coupled to communication circuitry, and is configured to provide wireless communications, in conjunction with the communications circuitry, between the implantable medical device and one or more external devices.

2. The device of claim 1, wherein the antenna comprises a circular cylindrical shape.

3. The device of claim 1, wherein the first side of the antenna is located adjacent to the top surface of the power source.

4. The device of claim 1, wherein the second side of the antenna is located adjacent to a circuit package that includes the electronic circuitry.

5. The device of claim 1, wherein an outside dimension of the antenna winding is a diameter comprising a dimensional value that is less than a dimensional value of an inside diameter of a case portion of the implantable medical device surrounding the antenna along the outside dimension of the antenna.

6. The device of claim 1, wherein the antenna winding comprises a pair of rectangular portions in cross-section that surround the passageway to form a circular cylindrical shaped passageway.

7. The device of claim 1, wherein a shape of the power connection is a same shape as a cross-sectional shape of the passageway.

8. The device of claim 1, wherein the power connection comprises a resilient member included within the power connection, the resilient member configured to urge a contact tip of the power connection in a direction through the passageway and toward an electrical contact pad that is electrically coupled to the electronic circuitry.

9. The device of claim 1, wherein the antenna winding is formed from an electrical conductor comprising a copper magnetic wire.

10. The device of claim 1, wherein antenna winding has an outside diameter perpendicular to the longitudinal axis of the antenna of less than 5.5 mm.

11. The device of claim 1, wherein the implantable medical device is configured to be implanted within a ventricle of a heart of a patient and to provide electrical therapy to the patient via by a plurality of electrodes.

12. The device of claim 1, wherein the antenna is configured to operate at a frequency up to 175 kHz.

13. A communication device for an implantable medical device, the communication device comprising:

an antenna comprising an axially symmetrical antenna winding comprising a plurality of windings of an electrical conductor surrounding a longitudinal axis of the antenna; and a passageway extending through the antenna winding along the longitudinal axis from a first side of the antenna to a second side of the antenna opposite the first side, the passageway configured to receive a power connection at the first side of the antenna and to provide a pathway for the power connection to extend through the passageway to electrically couple the power connection to an electronic circuitry located on the second side of the antenna, wherein the antenna is coupled to communication circuitry, and is configured to provide wireless communications, in conjunction with the communications circuitry, between the implantable medical device and one or more external devices.

14. The device of claim 13, wherein the antenna comprises a Brooks coil.

15. The device of claim 13, wherein the antenna winding has and outside coil diameter of less than 5.5 millimeters.

16. The device of claim 13, wherein the antenna winding comprises a number of turns of the electrical conductor in a range of 466 to 550 turns.

17. The device of claim 13, wherein the antenna winding comprises a coil providing an inductance of 757 to 1055 µH at an operating frequency of up to 175 kHz.

18. The device of claim 13, wherein the antenna winding is formed using 45 AWG copper magnet wire.

19. The device of claim 13, wherein the antenna winding is formed using 50 AWG copper magnet wire.

20. The device of claim 13, wherein the antenna comprises a radius, the radius comprising a dimensional value measured between the longitudinal axis of the antenna winding and a midpoint of the thickness of the antenna winding, the thickness of the antenna winding comprising a dimensional value equal to two-thirds of the dimensional value of the radius.

21. The device of claim 13, wherein the antenna winding is formed on a coil form the encloses one or more sides of the antenna winding.

22. The device of claim 13, wherein the antenna winding is formed of a plurality of layers of windings of the electrical conductor, each layer including a plurality of individual windings of the electrical conductor, wherein each individual winding of the plurality of individual windings is formed at a distance from the longitudinal axis of the antenna that is approximately the same as a distance of each other individual winding of the plurality of individual windings in the same layer of the plurality of layers.

23. A method for operating an implantable medical device implanted within a patient, the method comprising:

receiving electrical power, by a power connection, from a power source within the implanted medical device to power the electronic circuitry located within the implantable medical device, the power connection coupled to an electrical terminal of the power source and to the electronic circuitry; and providing, by an antenna coupled to communication circuitry, wireless communications, in conjunction with the communication circuitry, between the implantable medical device and one or more external devices using a signal that is transmitted from the antenna of the implanted medical device or that is received by the antenna of the implantable medical device;

wherein the antenna comprises an axially symmetrical antenna winding that at least partially surrounds a passageway extending through the antenna winding along a longitudinal axis of the antenna and wherein the power connection electrically coupled to the electrical terminal of the power source extends from a top surface of the power source into the passageway on a first side of the antenna and forms an electrical connection with the electronic circuitry, including the communication circuitry, located on a second side of the antenna opposite the first side of the antenna.

24. The method of claim 23, wherein the antenna comprises a circular cylindrical shape.

25. The method of claim 23, wherein the first side of the antenna is located adjacent to the top surface of the power source, and wherein the second side of the antenna is located adjacent to a circuit package that includes the electronic circuitry.

26. The method of claim 23, wherein an outside dimension of the antenna winding is a diameter comprising a dimensional value that is less than a dimensional value of an inside diameter of a case portion of the implantable medical device surrounding the antenna along the outside dimension of the antenna.

27. The method of claim 23, wherein the antenna winding comprises a pair of rectangular portions in cross-section that surround the passageway to form a circular cylindrical shaped passageway.

28. The method of claim 23, wherein a shape of the power connection is a same shape as a cross-sectional shape of the passageway.

29. The method of claim 23, wherein the power connection comprises a resilient member included within the power connection, the resilient member configured to urge a contact tip of the power connection in a direction through the passageway and toward an electrical contact pad that is electrically coupled to the electronic circuitry.

30. The method of claim 23, wherein the antenna winding is formed from an electrical conductor comprising a copper magnetic wire.

31. The method of claim 23, wherein antenna winding has an outside diameter perpendicular to the longitudinal axis of the antenna of less than 5.5 mm.

32. The method of claim 23, wherein providing wireless communications between the implantable medical device and the one or more external devices comprises providing wireless communications using a radio frequency communication link.

33. The method of claim 32, wherein the antenna is configured to operate at a frequency up to 175 kHz.

34. The method of claim 23, wherein receiving electrical power from the power source comprises operating the implantable medical device without recharging the power source throughout a timespan that the implantable medical device remains implanted within the patient.

35. A method for assembling an implantable medical device, comprising:
    attaching an antenna winding to a circuit package including electronic circuitry, the antenna winding comprising a wound electrical conductor surrounding a passageway extending through the antenna winding along a longitudinal axis of the antenna; and
    advancing the antenna winding and the circuit package toward an electrical power source including an electrical power connection extending from a top surface of the electrical power source so that the electrical power connection advances into the passageway of the antenna winding to form an electrical coupling with the electronic circuitry,
    wherein advancing the antenna winding toward the electrical power source includes advancing a bottom surface of the antenna toward the top surface of the electrical power source.

36. The method of claim 35,
    wherein the antenna winding is formed in a circular cylindrical shape, and
    wherein the passageway is formed in a circular cylindrical shape included within the antenna winding and comprising an outside diameter of the passageway forming a side that is surrounded by the antenna winding.

37. The method of claim 35, wherein the antenna comprises a Brooks coil.

* * * * *